(12) United States Patent
Van Arkel et al.

(10) Patent No.: US 10,467,379 B2
(45) Date of Patent: Nov. 5, 2019

(54) NEAR REAL-TIME DETECTION OF INFORMATION

(71) Applicant: Verizon Patent and Licensing Inc., Arlington, VA (US)

(72) Inventors: John H. Van Arkel, Colorado Springs, CO (US); James J. Wagner, Colorado Springs, CO (US); Corrine L. Schweyen, Columbus, OH (US); Saralyn M. Mahone, Colorado Springs, OH (US); David D. Tada, Colorado Springs, CO (US); Terrill J. Curtis, Pueblo West, CO (US); Scott Hagins, Colorado Springs, CO (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 603 days.

(21) Appl. No.: 14/841,092

(22) Filed: Aug. 31, 2015

(65) Prior Publication Data
US 2015/0370978 A1    Dec. 24, 2015

Related U.S. Application Data

(63) Continuation-in-part of application No. 13/536,367, filed on Jun. 28, 2012, now abandoned.

(60) Provisional application No. 61/503,339, filed on Jun. 30, 2011.

(51) Int. Cl.
*G06Q 40/08* (2012.01)
*G06F 19/00* (2018.01)
*G06Q 10/10* (2012.01)

(52) U.S. Cl.
CPC .......... *G06F 19/328* (2013.01); *G06Q 10/10* (2013.01)

(58) Field of Classification Search
CPC ...................................................... G06Q 40/08
See application file for complete search history.

(56) References Cited

U.S. PATENT DOCUMENTS

| | | |
|---|---|---|
| 2003/0115195 A1 | 6/2003 | Fogel et al. |
| 2003/0229519 A1 | 12/2003 | Eidex et al. |
| 2005/0276401 A1 | 12/2005 | Madill, Jr. et al. |
| 2006/0217824 A1* | 9/2006 | Allmon ................. G06F 19/328 700/90 |
| 2008/0249820 A1 | 10/2008 | Pathria et al. |

(Continued)

OTHER PUBLICATIONS

"Medicare Claims Processing Manual, Chapter 27—CWF Edit Resolution Procedures" Section 20.2.1.3—"Cancel/Void Acepted"; Jun. 22, 2013 (Year: 2003).*

(Continued)

*Primary Examiner* — John A Pauls

(57) ABSTRACT

A device may identify information associated with other devices, generate a first value for one or more indicators associated with the information, process, based on providing the information to a rules engine corresponding to a library of rules including the rule and receiving, from the rules engine and based on providing the information to the rules engine, information associated with a second value the information using a rule to generate the second value based on combining the first value with one or more third values, and output information regarding the second value to determine how to process the information.

20 Claims, 13 Drawing Sheets

(56) References Cited

U.S. PATENT DOCUMENTS

2009/0099884 A1 4/2009 Hoefelmeyer et al.
2009/0254379 A1 10/2009 Adams et al.

OTHER PUBLICATIONS

Liles et al., "Predictive Modeling in Medical Billing: The Latest Advance id Sophisticated Data Mining Techniques are Enabling ZPICs and Law Enforcement to Identify Fraud Sooner and Prevent it from Continuing" Apr. 19, 2011, 3 pages.
Medicare Program Integrity Manual Chapter 1—Medicare Improper Payments: Measuring, Correcting, and Preventing Overpayments and Underpayments, CMS, Nov. 20, 2009, 14 pages.
Medicare Program Integrity Manual Chapter 2—Data Analysis, CMS, Nov. 20, 2009, 10 pages.
Medicare Program Integrity Manual Chapter 4—Benefit Integrity, CMS, Nov. 20, 2009, 177 pages.

* cited by examiner

US 10,467,379 B2

NEAR REAL-TIME DETECTION OF INFORMATION

RELATED APPLICATION

This application is a continuation-in-part of U.S. patent application Ser. No. 13/536,367, filed Jun. 28, 2012, which claims priority under 35 U.S.C. § 119 based on U.S. Provisional Patent Application No. 61/503,339, filed Jun. 30, 2011, the disclosures of which are incorporated by reference herein in their entireties.

BACKGROUND

Healthcare fraud is a sizeable and significant challenge for the healthcare and insurance industries, and costs these industries billions of dollars each year. Healthcare fraud is a significant threat to most healthcare programs, such as government sponsored programs and private programs. Currently, healthcare providers, such as doctors, pharmacies, hospitals, etc., provide healthcare services to beneficiaries, and submit healthcare claims for the provision of such services. The healthcare claims are provided to a clearinghouse that makes minor edits to the claims, and provides the edited claims to a claims processor. The claims processor, in turn, processes, edits, and/or pays the healthcare claims. The clearinghouse and/or the claims processor may be associated with one or more private or public health insurers and/or other healthcare entities.

After paying the healthcare claims, the claims processor forwards the paid claims to a zone program integrity contractor. The zone program integrity contractor reviews the paid claims to determine whether any of the paid claims are fraudulent. A recovery audit contractor may also review the paid claims to determine whether any of them are fraudulent. In one example, the paid claims may be reviewed against a black list of suspect healthcare providers. If the zone program integrity contractor or the recovery audit contractor discovers a fraudulent healthcare claim, they may attempt to recover the monies paid for the fraudulent healthcare claim. However, such after-the-fact recovery methods (e.g., pay and chase methods) are typically unsuccessful since an entity committing the fraud may be difficult to locate due to the fact that the entity may not be a legitimate person, organization, business, etc. Furthermore, relying on law enforcement agencies to track down and prosecute such fraudulent entities may prove fruitless since law enforcement agencies lack the resources to handle healthcare fraud and it may require a long period of time to build a case against the fraudulent entities.

DETAILED DESCRIPTION OF PREFERRED EMBODIMENTS

The following detailed description refers to the accompanying drawings. The same reference numbers in different drawings may identify the same or similar elements.

An implementation, described herein, may detect a fraudulent healthcare claim, from a provider, by providing healthcare fraud detection tools and claims review processes in a near real-time pre-payment model and by rapidly adapting the fraud detection tools and practices as an environment changes. In one implementation, when a healthcare claim is determined to be fraudulent, the claim may be denied or challenged prior to payment by a claims processor. Alternatively, or additionally, a type, such as a physician provider claim, an institutional claim, etc., associated with the healthcare claim may be determined, and rules may be selected for the healthcare claim based on the type of claim. The healthcare claim may be processed using the selected rules, and alarms, generated by the processed healthcare claim, may be collected and sorted. The alarms may be analyzed, a fraud score for the healthcare claim may be calculated based on the alarm analysis, and an alert (e.g., permitting or denying the claim) and/or reports may generated based on the calculated fraud score for the healthcare claim.

Figure 1:
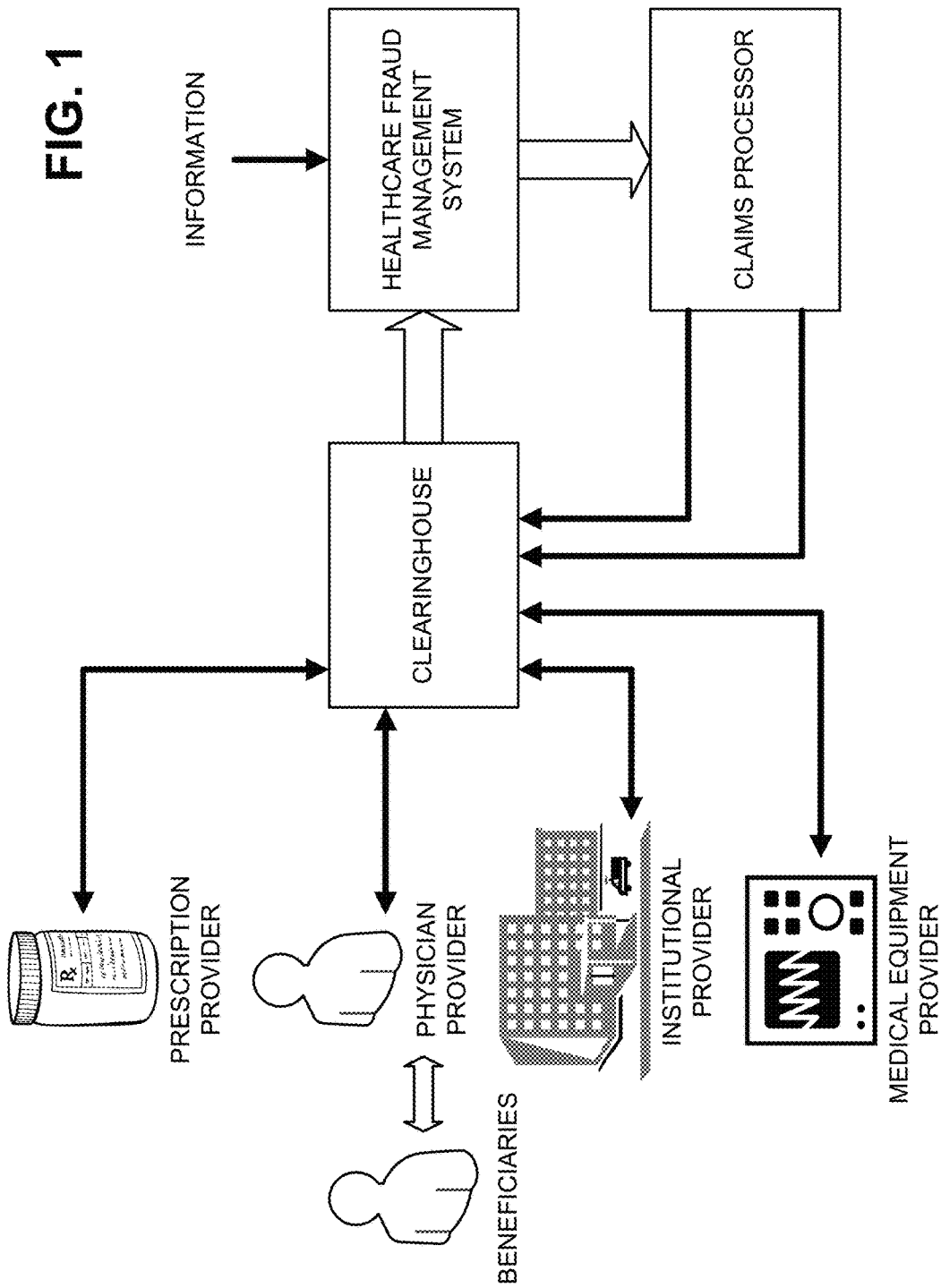
FIG. 1 is a diagram of an overview of an implementation described herein.

FIG. 1 is a diagram of an overview of an implementation described herein. For the example of FIG. 1, assume that beneficiaries receive healthcare services from a provider, such as a prescription provider, a physician provider, an institutional provider, a medical equipment provider, etc. The term "beneficiary," as used herein, is intended to be broadly interpreted to include a member, a person, a business, an organization, or some other type of entity that receives healthcare services, such as prescription drugs, surgical procedures, doctor's office visits, physicals, hospital care, medical equipment, etc. from a provider. The term "provider," as used herein, is intended to be broadly interpreted to include a prescription provider (e.g., a drug store, a pharmaceutical company, an online pharmacy, a brick and mortar pharmacy, etc.), a physician provider (e.g., a doctor, a surgeon, a physical therapist, a nurse, a nurse assistant, etc.), an institutional provider (e.g., a hospital, a medical emergency center, a surgery center, a trauma center, a clinic, etc.), a medical equipment provider (e.g., diagnostic equipment provider, a therapeutic equipment provider, a life support equipment provider, a medical monitor provider, a medical laboratory equipment provider, a home health agency, etc.), etc.

After providing the healthcare services, the provider may submit claims to a clearinghouse. The terms "claim" or "healthcare claim," as used herein, are intended to be broadly interpreted to include an interaction of a provider with a clearinghouse, a claims processor, or another entity responsible for paying for a beneficiary's healthcare or medical expenses, or a portion thereof. The interaction may involve the payment of money, a promise for a future payment of money, the deposit of money into an account, or the removal of money from an account. The term "money," as used herein, is intended to be broadly interpreted to include anything that can be accepted as payment for goods or services, such as currency, coupons, credit cards, debit cards, gift cards, and funds held in a financial account (e.g., a checking account, a money market account, a savings account, a stock account, a mutual fund account, a paypal account, etc.). The clearinghouse may make minor changes to the claims, and may provide information associated with the claims, such as provider information, beneficiary information, healthcare service information, etc., to a healthcare fraud management system.

In one implementation, each healthcare claim may involve a one time exchange of information, between the clearinghouse and the healthcare fraud management system, which may occur in near real-time to submission of the claim to the clearinghouse and prior to payment of the claim. Alternatively, or additionally, each healthcare claim may involve a series of exchanges of information, between the clearinghouse and the healthcare fraud management system, which may occur prior to payment of the claim.

The healthcare fraud management system may receive the claims information from the clearinghouse and may obtain other information regarding healthcare fraud from other systems. For example, the other healthcare fraud information may include information associated with providers under investigation for possible fraudulent activities, information associated with providers who previously committed fraud, information provided by zone program integrity contractors (ZPICs), information provided by recovery audit contractors, etc. The information provided by the zone program integrity contractors may include cross-billing and relationships among healthcare providers, fraudulent activities between Medicare and Medicaid claims, whether two insurers are paying for the same services, amounts of services that providers bill, etc. The recovery audit contractors may provide information about providers whose billings for services are higher than the majority of providers in a community, information regarding whether beneficiaries received healthcare services and whether the services were medically necessary, information about suspended providers, information about providers that order a high number of certain items or services, information regarding high risk beneficiaries, etc. The healthcare fraud management system may use the claims information and the other information to facilitate the processing of a particular claim. In one example implementation, the healthcare fraud management system may not be limited to arrangements such as Medicare (private or public) or other similar mechanisms used in the private industry, but rather may be used to detect fraudulent activities in any healthcare arrangement.

For example, the healthcare fraud management system may process the claim using sets of rules, selected based on information relating to a claim type and the other information, to generate fraud information. The healthcare fraud management system may output the fraud information to the claims processor to inform the claims processor whether the particular claim potentially involves fraud. The fraud information may take the form of a fraud score or may take the form of an "accept" alert (meaning that the particular claim is not fraudulent) or a "reject" alert (meaning that the particular claim is potentially fraudulent or that "improper payments" were paid for the particular claim). The claims processor may then decide whether to pay the particular claim or challenge/deny payment for the particular claim based on the fraud information.

In some scenarios, the healthcare fraud management system may detect potential fraud in near real-time (i.e., while the claim is being submitted and/or processed). In other scenarios, the healthcare fraud management system may detect potential fraud after the claim is submitted (perhaps minutes, hours, or days later) but prior to payment of the claim. In either scenario, the healthcare fraud management system may reduce financial loss contributable to healthcare fraud. In addition, the healthcare fraud management system may help reduce health insurer costs in terms of software, hardware, and personnel dedicated to healthcare fraud detection and prevention.

Figure 2:
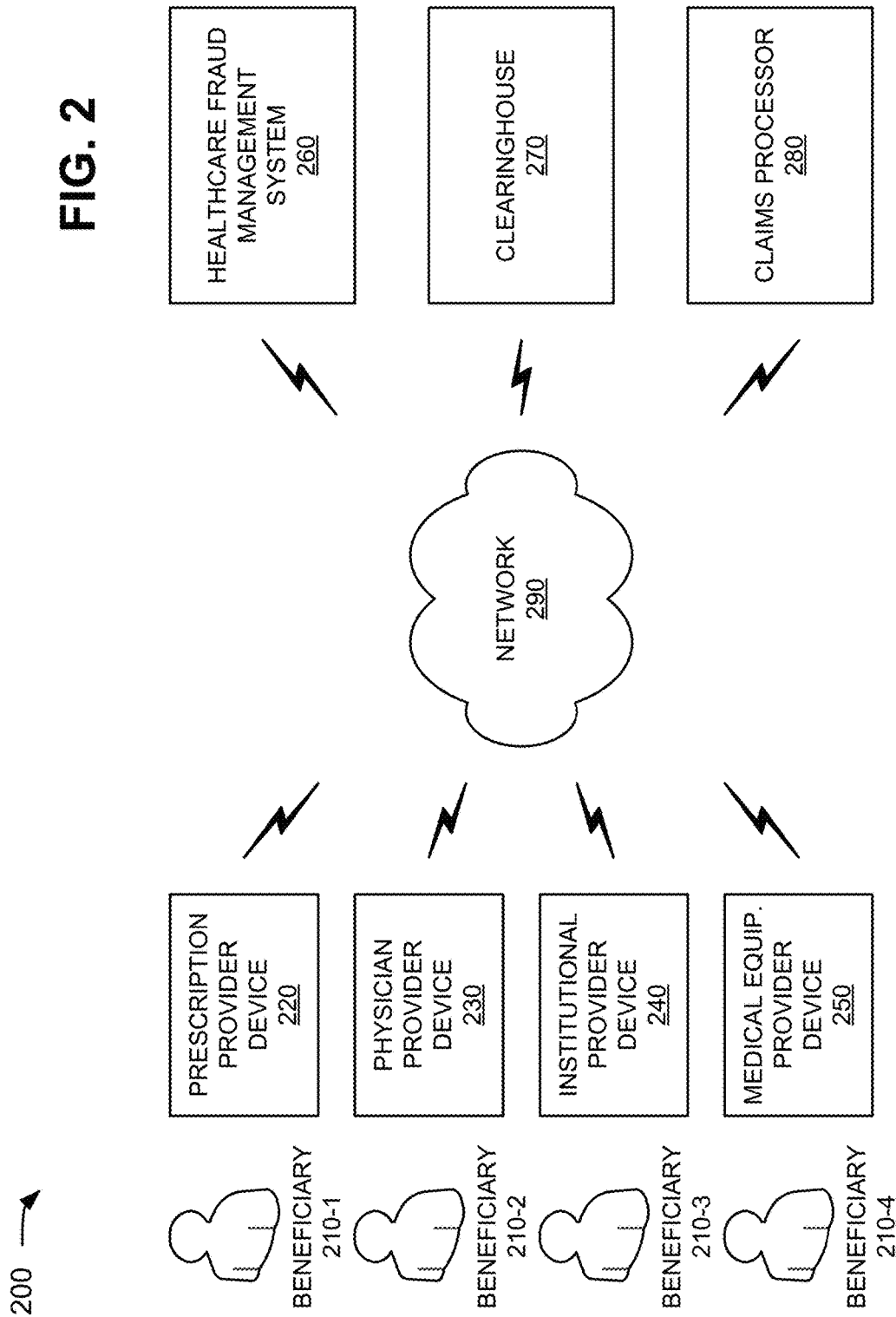
FIG. 2 is a diagram that illustrates an example environment in which systems and/or methods, described herein, may be implemented.

FIG. 2 is a diagram that illustrates an example environment 200 in which systems and/or methods, described herein, may be implemented. As shown in FIG. 2, environment 200 may include beneficiaries 210-1, . . . , 210-4 (collectively referred to as "beneficiaries 210," and individually as "beneficiary 210"), a prescription provider device 220, a physician provider device 230, an institutional provider device 240, a medical equipment provider device 250, a healthcare fraud management system 260, a clearinghouse 270, a claims processor 280, and a network 290.

While FIG. 2 shows a particular number and arrangement of devices, in practice, environment 200 may include additional devices, fewer devices, different devices, or differently arranged devices than are shown in FIG. 2. Also, although certain connections are shown in FIG. 2, these connections are simply examples and additional or different connections may exist in practice. Each of the connections may be a wired and/or wireless connection. Further, each prescription provider device 220, physician provider device 230, institutional provider device 240, and medical equipment provider device 250 may be implemented as multiple, possibly distributed, devices.

Beneficiary 210 may include a person, a business, an organization, or some other type of entity that receives healthcare services, such as services provided by a prescription provider, a physician provider, an institutional provider, a medical equipment provider, etc. For example, beneficiary 210 may receive prescription drugs, surgical procedures, doctor's office visits, physicals, hospital care, medical equipment, etc. from one or more providers.

Prescription provider device 220 may include a device, or a collection of devices, capable of interacting with clearinghouse 270 to submit a healthcare claim associated with healthcare services provided to a beneficiary 210 by a prescription provider. For example, prescription provider device 220 may correspond to a communication device (e.g., a mobile phone, a smartphone, a personal digital assistant (PDA), or a wireline telephone), a computer device (e.g., a laptop computer, a tablet computer, or a personal computer), a gaming device, a set top box, or another type of communication or computation device. As described herein, a prescription provider may use prescription provider device 220 to submit a healthcare claim to clearinghouse 270.

Physician provider device 230 may include a device, or a collection of devices, capable of interacting with clearinghouse 270 to submit a healthcare claim associated with healthcare services provided to a beneficiary 210 by a physician provider. For example, physician provider device 230 may correspond to a computer device (e.g., a server, a laptop computer, a tablet computer, or a personal computer).

Additionally, or alternatively, physician provider device 230 may include a communication device (e.g., a mobile phone, a smartphone, a PDA, or a wireline telephone) or another type of communication or computation device. As described herein, a physician provider may use physician provider device 230 to submit a healthcare claim to clearinghouse 270.

Institutional provider device 240 may include a device, or a collection of devices, capable of interacting with clearinghouse 270 to submit a healthcare claim associated with healthcare services provided to a beneficiary 210 by an institutional provider. For example, institutional provider device 240 may correspond to a computer device (e.g., a server, a laptop computer, a tablet computer, or a personal computer). Additionally, or alternatively, institutional provider device 240 may include a communication device (e.g., a mobile phone, a smartphone, a PDA, or a wireline telephone) or another type of communication or computation device. As described herein, an institutional provider may use institutional provider device 240 to submit a healthcare claim to clearinghouse 270.

Healthcare fraud management system 260 may include a device, or a collection of devices, that performs fraud analysis on healthcare claims in near real-time. Healthcare fraud management system 260 may receive claims information from clearinghouse 270, may receive other healthcare information from other sources, may perform fraud analysis with regard to the claims information and in light of the other information and claim types, and may provide, to claims processor 280, information regarding the results of the fraud analysis.

In one implementation, healthcare fraud management system 260 may provide near real-time fraud detection tools with predictive modeling and risk scoring, and may provide end-to-end case management and claims review processes. Healthcare fraud management system 260 may also provide comprehensive reporting and analytics. Healthcare fraud management system 260 may monitor healthcare claims, prior to payment, in order to detect fraudulent activities before claims are forwarded to adjudication systems, such as claims processor 280.

Clearinghouse 270 may include a device, or a collection of devices, that receives healthcare claims from a provider, such as one of provider devices 220-250, makes minor edits to the claims, and provides the edited claims to healthcare fraud management system 260 or to claims processor 280 and then to healthcare fraud management system 260. In one example, clearinghouse 270 may receive a healthcare claim from one of provider devices 220-250, and may check the claim for minor errors, such as incorrect beneficiary information, incorrect insurance information, etc. Once the claim is checked and no minor errors are discovered, clearinghouse 270 may securely transmit the claim to healthcare fraud management system 260.

Claims processor 280 may include a device, or a collection of devices, that receives a claim, and information regarding the results of the fraud analysis for the claim, from healthcare fraud management system 260. If the fraud analysis indicates that the claim is not fraudulent, claims processor 280 may process, edit, and/or pay the claim. However, if the fraud analysis indicates that the claim may be fraudulent, claims processor 280 may deny the claim and may perform a detailed review of the claim. The detailed analysis of the claim by claims processor 280 may be further supported by reports and other supporting documentation provided by healthcare fraud management system 260.

Network 290 may include any type of network or a combination of networks. For example, network 290 may include a local area network (LAN), a wide area network (WAN) (e.g., the Internet), a metropolitan area network (MAN), an ad hoc network, a telephone network (e.g., a Public Switched Telephone Network (PSTN), a cellular network, or a voice-over-IP (VoIP) network), an optical network (e.g., a FiOS network), or a combination of networks. In one implementation, network 290 may support secure communications between provider devices 220-250, healthcare fraud management system 260, clearinghouse 270, and/or claims processor 280. These secure communications may include encrypted communications, communications via a private network (e.g., a virtual private network (VPN) or a private IP VPN (PIP VPN)), other forms of secure communications, or a combination of secure types of communications.

Figure 3:
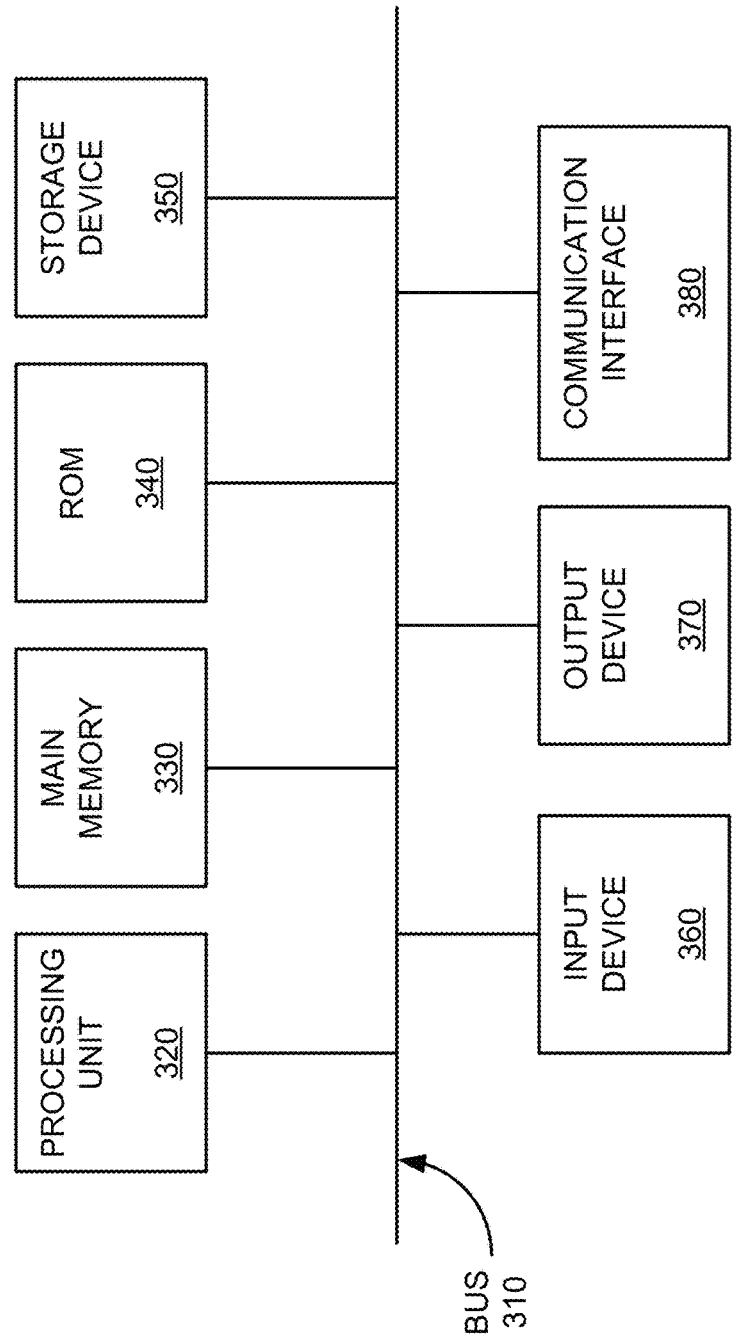
FIG. 3 is a diagram of example components of a device that may be used within the environment of FIG. 2.

FIG. 3 is a diagram of example components of a device 300. Device 300 may correspond to prescription provider device 220, physician provider device 230, institutional provider device 240, medical equipment provider device 250, healthcare fraud management system 260, clearinghouse 270, or claims processor 280. Each of prescription provider device 220, physician provider device 230, institutional provider device 240, medical equipment provider device 250, healthcare fraud management system 260, clearinghouse 270, and claims processor 280 may include one or more devices 300. As shown in FIG. 3, device 300 may include a bus 310, a processor 320, a main memory 330, a read only memory (ROM) 340, a storage device 350, an input device 360, an output device 370, and a communication interface 380.

Bus 310 may include a path that permits communication among the components of device 300. Processor 320 may include one or more processors, one or more microprocessors, one or more application specific integrated circuits (ASICs), one or more field programmable gate arrays (FPGAs), or one or more other types of processors that interpret and execute instructions. Main memory 330 may include a random access memory (RAM) or another type of dynamic storage device that stores information or instructions for execution by processor 320. ROM 340 may include a ROM device or another type of static storage device that stores static information or instructions for use by processor 320. Storage device 350 may include a magnetic storage medium, such as a hard disk drive, or a removable memory, such as a flash memory.

Input device 360 may include a mechanism that permits an operator to input information to device 300, such as a control button, a keyboard, a keypad, or another type of input device. Output device 370 may include a mechanism that outputs information to the operator, such as a light emitting diode (LED), a display, or another type of output device. Communication interface 380 may include any transceiver-like mechanism that enables device 300 to communicate with other devices or networks (e.g., network 290). In one implementation, communication interface 380 may include a wireless interface and/or a wired interface.

Device 300 may perform certain operations, as described in detail below. Device 300 may perform these operations in response to processor 320 executing software instructions contained in a computer-readable medium, such as main memory 330. A computer-readable medium may be defined as a non-transitory memory device. A memory device may include space within a single physical memory device or spread across multiple physical memory devices.

The software instructions may be read into main memory 330 from another computer-readable medium, such as storage device 350, or from another device via communication interface 380. The software instructions contained in main memory 330 may cause processor 320 to perform processes that will be described later. Alternatively, hardwired circuitry may be used in place of or in combination with software instructions to implement processes described herein. Thus, implementations described herein are not limited to any specific combination of hardware circuitry and software.

Although FIG. 3 shows example components of device 300, in other implementations, device 300 may include fewer components, different components, differently arranged components, and/or additional components than those depicted in FIG. 3. Alternatively, or additionally, one or more components of device 300 may perform one or more tasks described as being performed by one or more other components of device 300.

Figure 4:
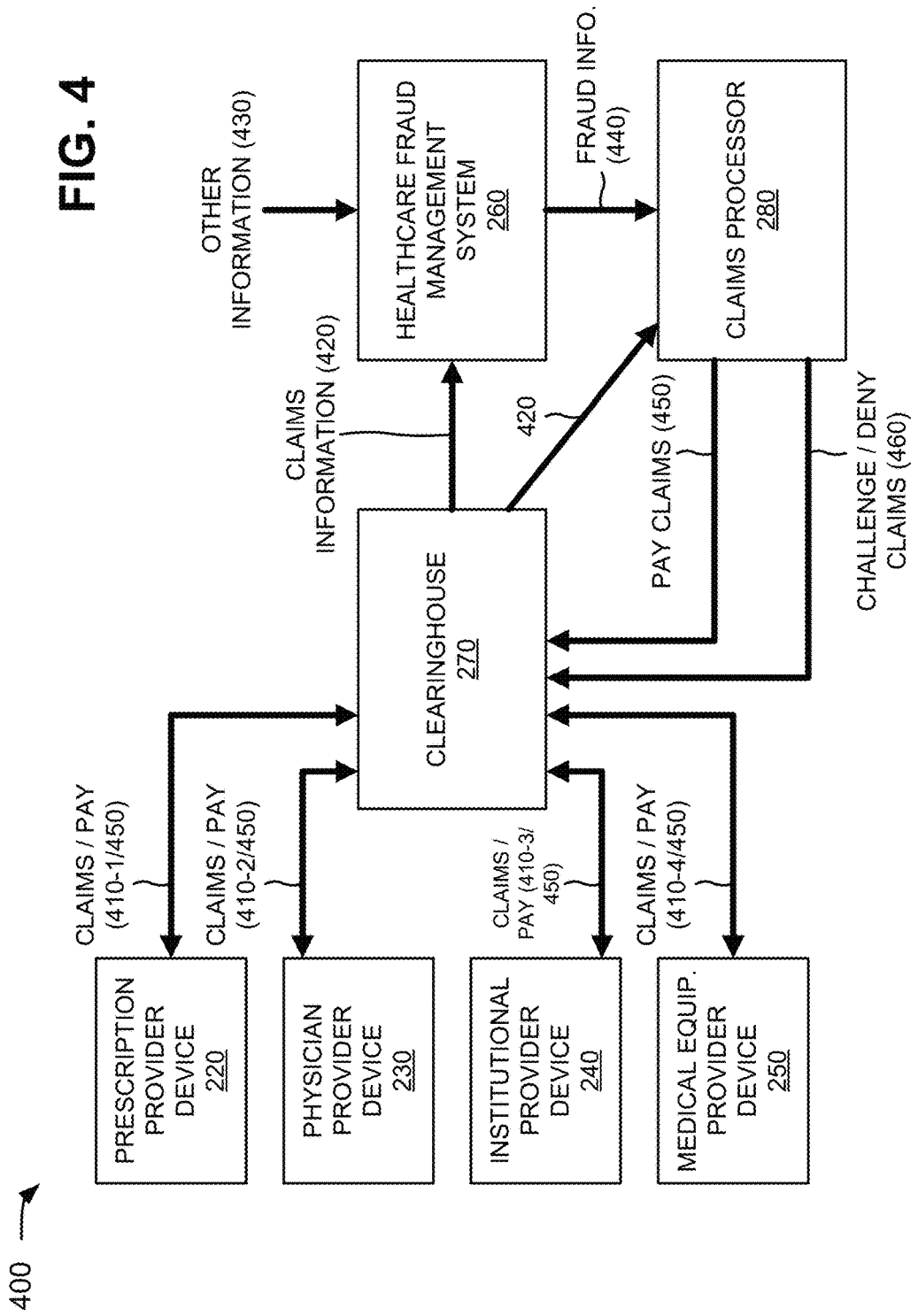
FIG. 4 is a diagram of example interactions between components of an example portion of the environment depicted in FIG. 2.

FIG. 4 is a diagram of example interactions between components of an example portion 400 of environment 200. As shown, example portion 400 may include prescription provider device 220, physician provider device 230, institutional provider device 240, medical equipment provider device 250, healthcare fraud management system 260, clearinghouse 270, and claims processor 280. Prescription provider device 220, physician provider device 230, institutional provider device 240, medical equipment provider device 250, healthcare fraud management system 260, clearinghouse 270, and claims processor 280 may include the features described above in connection with, for example, one or more of FIGS. 2 and 3.

Beneficiaries (not shown) may or may not receive healthcare services from a provider associated with prescription provider device 220, physician provider device 230, institutional provider device 240, and/or medical equipment provider device 250. As further shown in FIG. 4, whether or not the providers legitimately provided the healthcare services to the beneficiaries, prescription provider device 220 may generate claims 410-1, physician provider device 230 may generate claims 410-2, institutional provider device 240 may generate claims 410-3, and medical equipment provider device 250 may generate claims 410-4. Claims 410-1, . . . , 410-4 (collectively referred to herein as "claims 410," and, in some instances, singularly as "claim 410") may be provided to clearinghouse 270. Claims 410 may include interactions of a provider with clearinghouse 270, claims processor 280, or another entity responsible for paying for a beneficiary's healthcare or medical expenses, or a portion thereof. Claims 410 may be either legitimate or fraudulent.

Clearinghouse 270 may receive claims 410, may make minor changes to claims 410, and may provide claims information 420 to healthcare fraud management system 260 or to claims processor 280 and then to healthcare fraud management system 260. Claims information 420 may include provider information, beneficiary information, healthcare service information, etc. In one implementation, each claim 410 may involve a one-time exchange of information, between clearinghouse 270 and healthcare fraud management system 260, which may occur in near real-time to submission of claim 410 to clearinghouse 270 and prior to payment of claim 410. Alternatively, or additionally, each claim 410 may involve a series of exchanges of information, between clearinghouse 270 and healthcare fraud management system 260, which may occur prior to payment of claim 410.

Healthcare fraud management system 260 may receive claims information 420 from clearinghouse 270 and may obtain other information 430 regarding healthcare fraud from other systems. For example, other information 430 may include information associated with providers under investigation for possible fraudulent activities, information associated with providers who previously committed fraud, information provided by ZPICs, information provided by recovery audit contractors, and information provided by other external data sources. The information provided by the other external data sources may include an excluded provider list (EPL), a federal investigation database (FID), compromised provider and beneficiary identification (ID) numbers, compromised number contractor (CNC) information, benefit integrity unit (BIU) information, provider enrollment (PECOS) system information, and information from common working file (CWF) and claims adjudication systems. Healthcare fraud management system 260 may use claims information 420 and other information 430 to facilitate the processing of a particular claim 410.

For example, healthcare fraud management system 260 may process the particular claim 410 using sets of rules, selected based on information relating to a determined claim type and based on other information 430, to generate fraud information 440. Depending on the determined claim type associated with the particular claim 410, healthcare fraud management system 260 may select one or more of a procedure frequency rule, a geographical dispersion of services rule, a geographical dispersion of participants rule, a beneficiary frequency on provider rule, an auto summation of provider procedure time rule, a suspect beneficiary ID theft rule, an aberrant practice patterns rule, etc. Examples of such rules are described below in connection with FIG. 7. In one implementation, healthcare fraud management system 260 may process the particular claim 410 against a set of rules sequentially or in parallel. Healthcare fraud management system 260 may output fraud information 440 to claims processor 280 to inform claims processor 280 whether the particular claim 410 is potentially fraudulent. Fraud information 440 may include a fraud score, a fraud report, an "accept" alert (meaning that the particular claim 410 is not fraudulent), or a "reject" alert (meaning that the particular claim 410 is potentially fraudulent or improper payments were made for the particular claim). Claims processor 280 may then decide whether to pay the particular claim 410, as indicated by reference number 450, or challenge/deny payment for the particular claim 410, as indicated by reference number 460, based on fraud information 440.

In one implementation, healthcare fraud management system 260 may output fraud information 440 to clearinghouse 270 to inform clearinghouse 270 whether the particular claim 410 is potentially fraudulent. If fraud information 440 indicates that the particular claim 410 is fraudulent, clearinghouse 270 may reject the particular claim 410 and may provide an indication of the rejection to one of provider devices 220-250.

Alternatively, or additionally, healthcare fraud management system 260 may output (e.g., after payment of the particular claim 410) fraud information 440 to a claims recovery entity (e.g., a ZPIC or a recovery audit contractor) to inform the claims recovery entity whether the particular claim 410 is potentially fraudulent. If fraud information 440 indicates that the particular claim 410 is fraudulent, the claims recovery entity may initiate a claims recovery process to recover the money paid for the particular claim 410.

Although FIG. 4 shows example components of example portion 400, in other implementations, example portion 400 may include fewer components, different components, differently arranged components, and/or additional components than those depicted in FIG. 4. Alternatively, or additionally, one or more components of example portion 400 may perform one or more tasks described as being performed by one or more other components of example portion 400.

Figure 5:
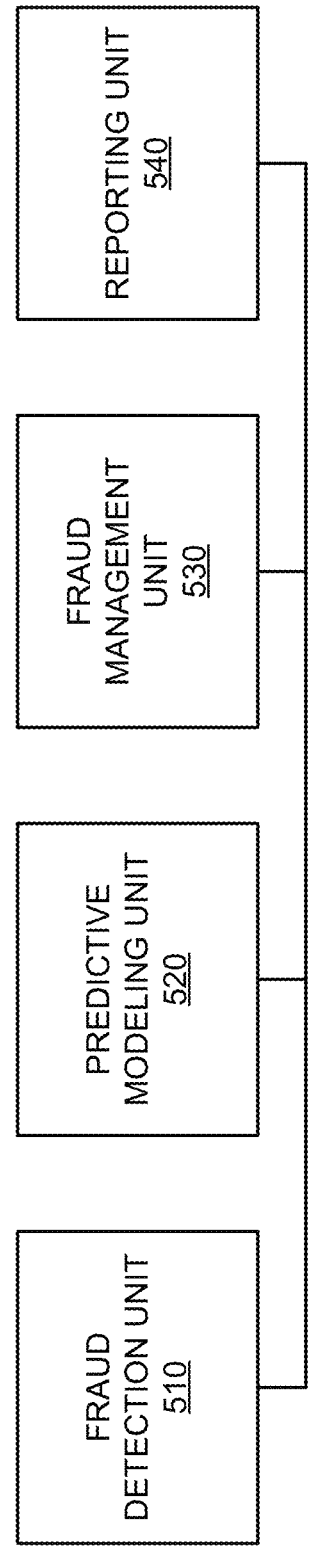
FIG. 5 is a diagram of example functional components of a healthcare fraud management system of FIG. 2.

FIG. 5 is a diagram of example functional components of healthcare fraud management system 260. In one implementation, the functions described in connection with FIG. 5 may be performed by one or more components of device 300 (FIG. 3) or by one or more devices 300. As shown in FIG. 5, healthcare fraud management system 260 may include a fraud detection unit 510, a predictive modeling unit 520, a fraud management unit 530, and a reporting unit 540. Fraud detection unit 510, predictive modeling unit 520, fraud management unit 530, and reporting unit 540 will be described generally with regard to FIG. 5 and will be described in more detail with regard to FIGS. 6-11.

Generally, fraud detection unit 510 may receive claims information 420 from clearinghouse 270, may receive other information 430 from other sources, and may analyze claims 410, in light of other information 430 and claim types, to determine whether claims 410 are potentially fraudulent. In one implementation, fraud detection unit 510 may generate a fraud score for a claim 410, and may classify a claim 410 as "safe," "unsafe," or "for review," based on the fraud score. A "safe" claim may include a claim 410 with a fraud score that is less than a first threshold (e.g., less than 5, less than 10, less than 20, etc. within a range of fraud scores of 0 to 100, where a fraud score of 0 may represent a 0% probability that claim 410 is fraudulent and a fraud score of 100 may represent a 100% probability that the claim is fraudulent). An "unsafe" claim may include a claim 410 with a fraud score that is greater than a second threshold (e.g., greater than 90, greater than 80, greater than 95, etc. within the range of fraud scores of 0 to 100) (where the second threshold is greater than the first threshold). A "for review" claim may include a claim 410 with a fraud score that is greater than a third threshold (e.g., greater than 50, greater than 40, greater than 60, etc. within the range of fraud scores of 0 to 100) and not greater than the second threshold (where the third threshold is greater than the first threshold and less than the second threshold). In one implementation, the first, second, and third thresholds and the range of potential fraud scores may be set by an operator of healthcare fraud management system 260. Alternatively, or additionally, the first, second, and/or third thresholds and/or the range of potential fraud scores may be set by clearinghouse 270 and/or claims processor 280. In this case, the thresholds and/or range may vary from clearinghouse-to-clearinghouse and/or from claims processor-to-claims processor. The fraud score may represent a probability that a claim is fraudulent.

If fraud detection unit 510 determines that a claim 410 is a "safe" claim, fraud detection unit 510 may notify claims processor 280 that claims processor 280 may safely approve, or alternatively fulfill, claim 410. If fraud detection unit 510 determines that a claim 410 is an "unsafe" claim, fraud detection unit 510 may notify claims processor 280 to take measures to minimize the risk of fraud (e.g., deny claim 410, request additional information from one or more provider devices 220-250, require interaction with a human operator, refuse to fulfill a portion of claim 410, etc.). Alternatively, or additionally, fraud detection unit 510 may provide information regarding the unsafe claim to predictive modeling unit 520 and/or fraud management unit 530 for additional processing of claim 410. If fraud detection unit 510 determines that a claim 410 is a "for review" claim, fraud detection unit 410 may provide information regarding claim 410 to predictive modeling unit 520 and/or fraud management unit 530 for additional processing of claim 410.

In one implementation, fraud detection unit 510 may operate within the claims processing flow between clearinghouse 270 and claims processor 280, without creating processing delays. Fraud detection unit 510 may analyze and investigate claims 410 in real time or near real-time, and may refer "unsafe" claims or "for review" claims to a fraud case management team for review by clinical staff. Claims 410 deemed to be fraudulent may be delivered to claims processor 280 (or other review systems) so that payment can be suspended, pending final verification or appeal determination.

Generally, predictive modeling unit 520 may receive information regarding certain claims 410 and may analyze these claims 410 to determine whether the certain claims 410 are fraudulent. In one implementation, predictive modeling unit 520 may provide a high volume, streaming data reduction platform for claims 410. Predictive modeling unit 520 may receive claims 410, in real time or near real-time, and may apply claim type-specific predictive models, configurable edit rules, artificial intelligence techniques, and/or fraud scores to claims 410 in order to identify inappropriate patterns and outliers.

With regard to data reduction, predictive modeling unit 520 may normalize and filter claims information 420 and/or other information 430 (e.g., to a manageable size), may analyze the normalized/filtered information, may prioritize the normalized/filtered information, and may present a set of suspect claims 410 for investigation. The predictive models applied by predictive modeling unit 520 may support linear pattern recognition techniques (e.g., heuristics, expert rules, etc.) and non-linear pattern recognition techniques (e.g., neural nets, clustering, artificial intelligence, etc.). Predictive modeling unit 520 may assign fraud scores to claims 410, may create and correlate alarms across multiple fraud detection methods, and may prioritize claims 410 (e.g., based on fraud scores) so that claims 410 with the highest risk of fraud may be addressed first.

Generally, fraud management unit 530 may provide a holistic, compliant, and procedure-driven operational architecture that enables extraction of potentially fraudulent healthcare claims for more detailed review. Fraud management unit 530 may refer potentially fraudulent claims to trained analysts who may collect information (e.g., from healthcare fraud management system 260) necessary to substantiate further disposition of the claims. Fraud management unit 530 may generate key performance indicators (KPIs) that measure performance metrics for healthcare fraud management system 260 and/or the analysts.

In one implementation, fraud management unit 530 may provide lists of prioritized healthcare claims under review with supporting aggregated data, and may provide alerts and associated events for a selected healthcare claim. Fraud management unit 530 may provide notes and/or special handling instructions for a provider and/or beneficiary associated with a claim under investigation. Fraud management unit 530 may also provide table management tools (e.g., thresholds, exclusions, references, etc.), account management tools (e.g., roles, filters, groups, etc.), and geographical mapping tools and screens (e.g., for visual analysis) for healthcare claims under review.

Generally, reporting unit 540 may generate comprehensive standardized and ad-hoc reports for healthcare claims analyzed by healthcare fraud management system 260. For example, reporting unit 540 may generate financial management reports, trend analytics reports, return on investment reports, KPI/performance metrics reports, intervention analysis/effectiveness report, etc. Reporting unit 540 may provide data mining tools and a data warehouse for performing trending and analytics for healthcare claims. Information provided in the data warehouse may include alerts and case management data associated with healthcare claims. Such information may be available to claims analysts for trending, post data analysis, and additional claims development, such as preparing a claim for submission to program safeguard contractors (PSCs) and other authorized entities. In one example, information generated by reporting unit 540 may be used by fraud detection unit 510 and predictive modeling unit 520 to update rules, predictive models, artificial intelligence techniques, and/or fraud scores generated by fraud detection unit 510 and/or predictive modeling unit 520.

Although FIG. 5 shows example functional components of healthcare fraud management system 260, in other implementations, healthcare fraud management system 260 may include fewer functional components, different functional components, differently arranged functional components, and/or additional functional components than those depicted in FIG. 5. Alternatively, or additionally, one or more functional components of healthcare fraud management system 260 may perform one or more tasks described as being performed by one or more other functional components of healthcare fraud management system 260.

Figure 6:
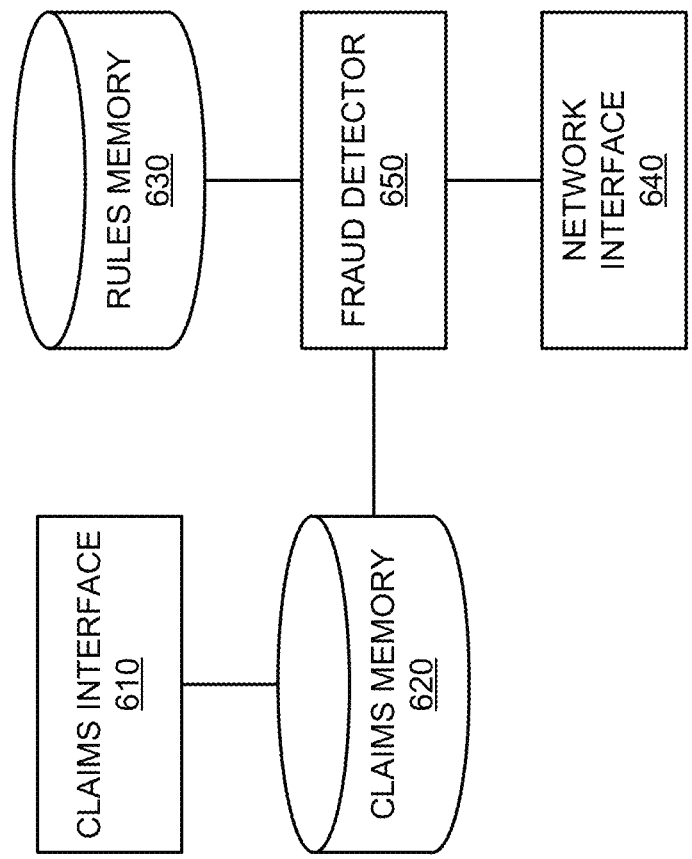
FIG. 6 is a diagram of example functional components of a fraud detection unit of FIG. 5.

FIG. 6 is a diagram of example functional components of fraud detection unit 510. In one implementation, the functions described in connection with FIG. 6 may be performed by one or more components of device 300 (FIG. 3) or by one or more devices 300. As shown in FIG. 6, fraud detection unit 510 may include a claims interface component 610, a claims memory 620, a rules memory 630, a network interface component 640, and a fraud detector component 650.

Claims interface component 610 may include a device, or a collection of devices, that may interact with clearinghouse 270 and claims processor 280 to assist the users of clearinghouse 270 and claims processor 280 in using healthcare fraud management system 260. For example, claims interface component 610 may exchange encryption information, such as public/private keys or VPN information, with clearinghouse 270 and/or claims processor 280 to permit secure future communications between healthcare fraud management system 260 and clearinghouse 270 and/or claims processor 280.

Claims interface component 610 may receive, from clearinghouse 270 or other systems, information that might be useful in detecting a fraudulent healthcare claim. For example, claims interface component 610 may receive claims information 420 from clearinghouse 270 and may obtain other information 430 regarding healthcare fraud from other systems. Other information 430 may include a black list (e.g., a list of beneficiaries or providers that are known to be associated with fraudulent activity) and/or a white list (e.g., a list of beneficiaries or providers that are known to be particularly trustworthy). Additionally, or alternatively, other information 430 may include historical records of claims associated with beneficiaries or providers. These historical records may include information regarding claims that were processed by a system other than healthcare fraud management system 260. Additionally, or alternatively, claims interface component 610 may receive a set of policies from clearinghouse 270 and/or claims processor 280. The policies may indicate thresholds for determining safe claims, unsafe claims, and for review claims, may indicate a range of possible fraud scores (e.g., range of 0 to 100, range of 0 to 1000, etc.), or may indicate other business practices of beneficiaries and/or providers. Additionally, or alternatively, claims interface component 610 may receive a set of rules that are particular to a beneficiary or a provider.

Claims memory 620 may include one or more memory devices to store information regarding present and/or past claims. Present claims may include claims currently being processed by fraud detector component 650, and past claims may include claims previously processed by fraud detector component 650. In one implementation, claims memory 620 may store data in the form of a database, such as a relational database or an object-oriented database. Alternatively, or additionally, claims memory 620 may store data in a non-database manner, such as as tables, linked lists, or another arrangement of data.

Claims memory 620 may store a variety of information for any particular claim. For example, claims memory 620 might store: information identifying a provider or one of provider devices 220-250 (e.g., a provider device ID, an IP address associated with the provider device, a telephone number associated with the provider device, a username associated with the provider, a provider ID, etc.); information identifying a beneficiary (e.g., a beneficiary ID, a beneficiary name, a beneficiary address, etc.); information identifying a type of provider (e.g., a prescription provider, a physician provider, an institutional provider, a medical equipment provider, etc.); a name, telephone number, and address associated with the provider; a dollar amount of the claim; line items of the claim (e.g., identification of each good/service purchased, healthcare procedure codes associated with the claim, etc.); information regarding insurance provided by a beneficiary (e.g., an insurance company name, an insurance company address, a group number, a medical record number, etc.); a day and/or time that the good/service associated with the claim was provided (e.g., 13:15 on Mar. 5, 2011); a geographic location associated with the beneficiary or the provider, and/or other types of information associated with the claim, the provider, one of provider devices 220-250, or the beneficiary, and/or past claims associated with the claim, the provider, one of provider devices 220-250, or the beneficiary.

Claims memory 620 may also store other information that might be useful in detecting a fraudulent healthcare claim. For example, claims memory 620 may store black lists and/or white lists. The black/white lists may be particular to a provider or a beneficiary or may be applicable across providers or beneficiaries. The black/white lists may be received from other systems or may be generated by healthcare fraud management system 260.

Claims memory 620 may also store historical records of claims from providers. These historical records may include claims that were processed by a system other than healthcare fraud management system 260. The historical records may include information similar to the information identified above and may also include information regarding claims that had been identified as fraudulent.

Rules memory 630 may include one or more memory devices to store information regarding rules that may be applicable to claims. In one implementation, rules memory 630 may store rules in one or more libraries. A "library" may be a block of memory locations (contiguous or non-contiguous memory locations) that stores a set of related rules.

Alternatively, or additionally, rules memory 630 may store rules in another manner (e.g., as database records, tables, linked lists, etc.).

The rules may include general rules, provider-specific rules, beneficiary-specific rules, claim attribute specific rules, single claim rules, multi-claim rules, heuristic rules, pattern recognition rules, and/or other types of rules. Some rules may be applicable to all claims (e.g., general rules may be applicable to all claims), while other rules may be applicable to a specific set of claims (e.g., provider-specific rules may be applicable to claims associated with a particular provider). Rules may be used to process a single claim (meaning that the claim may be analyzed for fraud without considering information from another claim) or may be used to process multiple claims (meaning that the claim may be analyzed for fraud by considering information from another claim). Rules may also be applicable for multiple, unaffiliated providers (e.g., providers having no business relationships) or multiple, unrelated beneficiaries (e.g., beneficiaries having no familial or other relationship).

Figure 7:
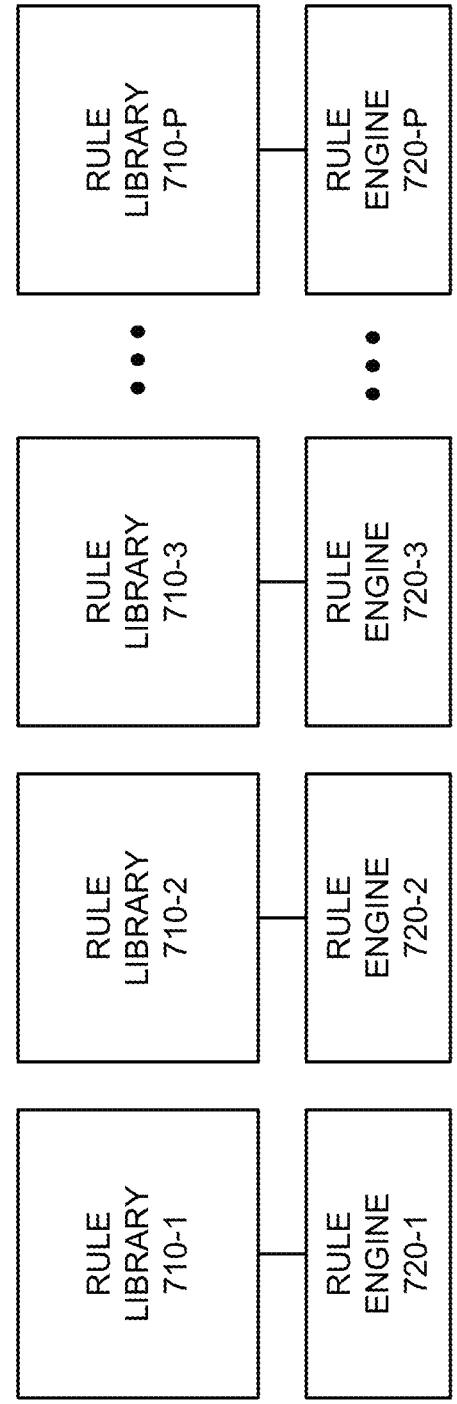
FIG. 7 is a diagram of example libraries that may be present within a rules memory of FIG. 6.

FIG. 7 is a diagram of example libraries that may be present within rules memory 630. As shown in FIG. 7, rules memory 630 may include rule libraries 710-1, 710-2, 710-3, . . . 710-P (P≥1) (collectively referred to as "libraries 710," and individually as "library 710") and rule engines 720-1, 720-2, 720-3, . . . 720-P (collectively referred to as "rule engines 720," and individually as "rule engine 720"). While FIG. 7 illustrates that rules memory 630 includes a set of rule libraries 710 and a corresponding set of rule engines 720, rules memory 630 may include fewer components, additional components, or different components in another implementation.

Each rule library 710 may store a set of related rules. For example, a rule library 710 may store general rules that are applicable to all claims. Additionally, or alternatively, a rule library 710 may store rules applicable to a single claim (meaning that the claim may be analyzed for fraud without considering information from another claim). Additionally, or alternatively, a rule library 710 may store rules applicable to multiple claims (meaning that the claim may be analyzed for fraud by considering information from another claim (whether from the same provider or a different provider, whether associated with the same beneficiary or a different beneficiary)).

Additionally, or alternatively, a rule library 710 may store provider-specific rules. Provider-specific rules may include rules that are applicable to claims of a particular provider, and not applicable to claims of other providers. Additionally, or alternatively, a rule library 710 may store provider type-specific rules. Provider type-specific rules may include rules that are applicable to claims associated with a particular type of provider (e.g., a prescription provider, a physician provider, an institutional provider, a medical equipment provider, etc.), and not applicable to claims associated with other types of providers. Additionally, or alternatively, a rule library 710 may store beneficiary-specific rules. Beneficiary-specific rules may include rules that are applicable to claims of a particular beneficiary or a particular set of beneficiaries (e.g., all beneficiaries in the beneficiary's family, all beneficiaries located at a particular geographic location, all beneficiaries located within a particular geographic region, etc.), and not applicable to claims of other beneficiaries or sets of beneficiaries.

Additionally, or alternatively, a rule library 710 may store procedure frequency-specific rules. Procedure frequency-specific rules may include rules that provide alerts for claims based on an excessive number (e.g., greater than a configurable threshold) of procedures or services performed for a single beneficiary in a configurable time period (e.g., a day, a week, a month, etc.). A priority associated with a claim may increase (e.g., indicating a more potentially fraudulent claim) as the number of procedures or services increases over the configurable threshold. Additionally, or alternatively, a rule library 710 may store geographical dispersion of services-specific rules. Geographical dispersion of services-specific rules may include rules that identify geographical anomalies between a beneficiary and providers based on time, distance, and frequency associated with a claim. Geographical dispersion of services-specific rules may provide alerts for a claim when a beneficiary receives a number of services (e.g., greater than a configurable threshold) from providers that are an improbable distance (e.g., greater than another threshold) from the beneficiary. A priority associated with a claim may increase (e.g., indicating a more potentially fraudulent claim) as a geographical dispersion between a beneficiary and a provider increases.

Additionally, or alternatively, a rule library 710 may store beneficiary frequency-specific rules. Beneficiary frequency-specific rules may include rules that provide alerts for claims when a single provider treats an excessive number (e.g., greater than a configurable threshold) of beneficiaries in a configurable time period (e.g., a day, a week, a month, etc.). A priority associated with a claim may increase (e.g., indicating a more potentially fraudulent claim) as the number of beneficiaries increases over the configurable threshold, as a variance from normal services provided by the provider increases, as a number of locations of the beneficiaries increases, etc.

Additionally, or alternatively, a rule library 710 may store single claim analysis-related rules. Single claim analysis-related rules may include rules that are applicable to suspected fraudulent providers and/or beneficiaries identified from sources, such as PECOs, EPL, vital statistics, etc. Additionally, or alternatively, a rule library 710 may store auto summation of provider procedure time-specific rules. Auto summation of provider procedure time-specific rules may include rules that identify a single provider who performs a number procedures that, when the procedure times are added together, exceed a probably work day for the provider. For example, the auto summation of provider procedure time-specific rules may identify a doctor who performs thirty (30) hours of surgery in a single day.

Additionally, or alternatively, a rule library 710 may store suspect beneficiary ID theft-specific rules. Suspect beneficiary ID theft-specific rules may include rules that identify a number of providers using the same beneficiary ID over a time period (e.g., a day, a week, etc.) but without specified place-of-service codes (e.g., hospital) and diagnosis codes. Suspect beneficiary ID theft-specific rules may include rules that identify a single beneficiary that receives an excessive number (e.g., greater than a configurable threshold by specialty) of procedures or services on the same day.

Additionally, or alternatively, a rule library 710 may store alert on suspect address-specific rules. Alert on suspect address-specific rules may include rules that correlate alerts based on national provider identifier (NPI) addresses to detect suspect addresses associated with providers and beneficiaries. Additionally, or alternatively, a rule library 710 may store inconsistent relationship-specific rules (e.g., a gynecological procedure performed on a male beneficiary), excessive cost-specific rules (e.g., costs for a beneficiary or a provider), etc.

Additionally, or alternatively, a rule library 710 may store rules that identify fraudulent therapies (e.g., physical therapy, occupational therapy, speech language pathology, psychotherapy, etc.) provided to groups of beneficiaries but which are claimed as if provided individually. Additionally, or alternatively, a rule library 710 may store rules that identify a "gang visit" fraud scheme. A gang visit may occur when providers (e.g., optometrists, podiatrists, etc.) visit most beneficiaries in a facility, without rendering any services, but bill as if services have been provided to all of the beneficiaries. Additionally, or alternatively, a rule library 710 may store rules that identify organized and coordinated healthcare fraud schemes, such as common surname origins for beneficiaries, a provider billing less than $10,000 per day, shared facilities among high risk providers, etc.

The rules in rule libraries 710 may include human-generated rules and/or automatically-generated rules. The automatically-generated rules may include heuristic rules and/or pattern recognition rules. Heuristic rules may include rules that have been generated by using statistical analysis, or the like, that involves analyzing a group of attributes (e.g., a pair of attributes or a tuple of attributes) of claims, and learning rules associated with combinations of attributes that are indicative of fraudulent claims. Pattern recognition rules may include rules that have been generated using machine learning, artificial intelligence, neural networks, decision trees, or the like, that analyzes patterns appearing in a set of training data, which includes information regarding claims that have been identified as fraudulent and information regarding claims that have been identified as non-fraudulent, and generates rules indicative of patterns associated with fraudulent claims.

Alternatively, or additionally, rule libraries 710 may store other types of rules, other combinations of rules, or differently-generated rules. Because fraud techniques are constantly changing, the rules, in rule libraries 710, may be regularly updated (either by manual or automated interaction) by modifying existing rules, adding new rules, and/or removing antiquated rules.

Each rule engine 720 may correspond to a corresponding rule library 710. A rule engine 720 may receive a claim from fraud detector component 650, coordinate the execution of the rules by the corresponding rule library 710, and return the results (in the form of zero or more alarms) to fraud detector component 650. In one implementation, rule engine 720 may cause a claim to be processed by a set of rules within the corresponding rule library 710 in parallel. In other words, the claim may be concurrently processed by multiple, different rules in a rule library 710 (rather than serially processed).

Returning to FIG. 6, network interface component 640 may include a device, or a collection of devices, that obtains, manages, and/or processes claims information 420 and other information 430, which may be used to facilitate the identification of fraudulent claims. Network interface component 640 may interact with clearinghouse 270 to obtain claims information 420, and may interact with other systems to obtain other information 430. In one implementation, network interface component 640 may store claims information 420 and other information 430 and perform look-ups within the stored information when requested by fraud detector component 650. Alternatively, or additionally, network interface component 640 may store claims information 420 and other information 430 and permit fraud detector component 650 to perform its own look-ups within the stored information. Network interface component 640 may store the information in the form of a database, such as a relational database or an object-oriented database. Alternatively, network interface component 640 may store the information in a non-database manner, such as as tables, linked lists, or another arrangement of data.

Fraud detector component 650 may include a device, or a collection of devices, that performs automatic fraud detection on claims. Fraud detector component 650 may receive a claim (e.g., associated with one of provider devices 220-250) from clearinghouse 270, obtain other information 430 relevant to the claim, and select particular libraries 710 and particular rules within the selected libraries 710 applicable to the claim based on other information 430 and a claim type. Fraud detector component 650 may then provide the claim for processing by the selected rules in the selected libraries 710 in parallel. The output of the processing, by the selected libraries 710, may include zero or more alarms. An "alarm," as used herein, is intended to be broadly interpreted as a triggering of a rule in a library 710. A rule is triggered when the claim satisfies the rule. For example, assume that a rule indicates a situation where a doctor performs a number of hours of services in single day. Claims for such work would trigger (or satisfy) the rule if the claims involved more than twenty-four (24) hours of services in single day.

Fraud detector component 650 may sort and group the alarms and analyze the groups to generate a fraud score. The fraud score may reflect the probability that the claim is fraudulent. Fraud detector component 650 may send the fraud score, or an alert generated based on the fraud score, to claims processor 280 via fraud information 440. The alert may simply indicate that claims processor 280 should pay, deny, or further review the claim. In one implementation, the processing by fraud detector component 650 from the time that fraud detector component 650 receives the claim to the time that fraud detector component 650 sends the alert may be within a relatively short time period, such as, for example, within thirty seconds, sixty seconds, or ten seconds. Alternatively, or additionally, the processing by fraud detector component 650 from the time that fraud detector component 650 receives the claim to the time that fraud detector component 650 sends the alert may be within a relatively longer time period, such as, for example, within minutes, hours, or days.

Although FIG. 6 shows example functional components of fraud detection unit 510, in other implementations, fraud detection unit 510 may include fewer functional components, different functional components, differently arranged functional components, and/or additional functional components than those depicted in FIG. 6. Alternatively, or additionally, one or more functional components of fraud detection unit 510 may perform one or more tasks described as being performed by one or more other functional components of fraud detection unit 510.

Figure 8:
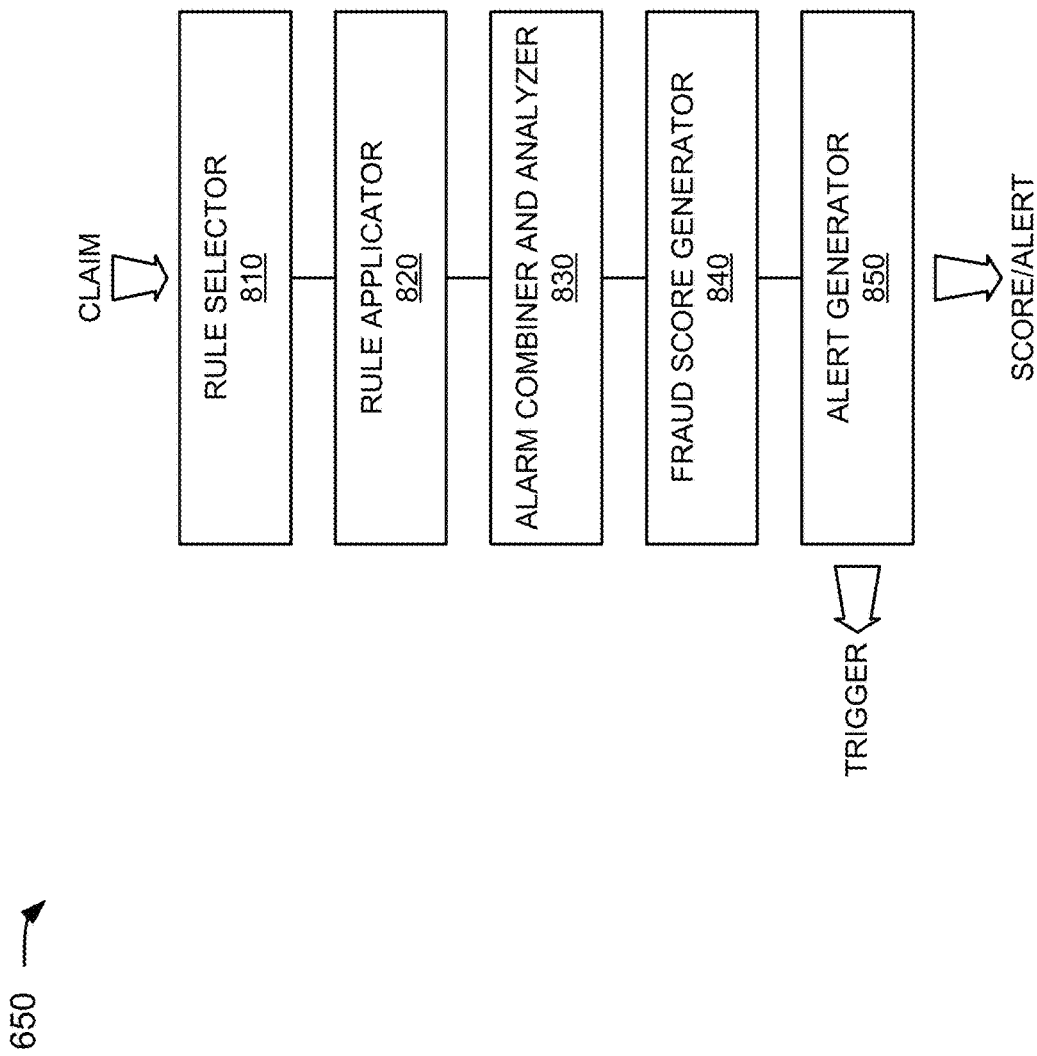
FIG. 8 is a diagram of example functional components of a fraud detector of FIG. 6.

FIG. 8 is a diagram of example functional components of fraud detector component 650. In one implementation, the functions described in connection with FIG. 8 may be performed by one or more components of device 300 (FIG. 3) or by one or more devices 300. As shown in FIG. 8, fraud detector component 650 may include a rule selector component 810, a rule applicator component 820, an alarm combiner and analyzer component 830, a fraud score generator component 840, and an alert generator component 850.

Rule selector component 810 may receive a claim 410 from clearinghouse 270 via claims information 420, and may determine a type (e.g., a prescription provider claim, a physician provider claim, an institutional provider claim, a medical equipment provider claim, etc.) associated with claim 410. In one implementation, claim 410 may include various information, such as information identifying a beneficiary (e.g., name, address, telephone number, etc.); a total dollar amount of claim 410; line items of claim 410 (e.g., information identifying a good or service purchased or rented, etc.); information identifying a provider (e.g., name, address, telephone number, etc.); and information identifying a day and/or time that claim 410 occurred or the services associated with claim 410 occurred (e.g., 13:15 on Apr. 5, 2011).

Additionally, or alternatively, rule selector component 810 may receive other information (called "meta information") from clearinghouse 270 in connection with claim 410. For example, the meta information may include information identifying one of provider devices 220-250 (e.g., a provider device ID, an IP address associated with the provider device, a telephone number associated with the provider device, etc.); other information regarding one of provider devices 220-250 (e.g., a type/version of browser used by the provider device, cookie information associated with the provider device, a type/version of an operating system used by the provider device, etc.); and/or other types of information associated with claim 410, the provider, the provider device, or the beneficiary.

Additionally, or alternatively, rule selector component 810 may receive or obtain other information 430 regarding claim 410, the provider, the provider device, or the beneficiary. For example, other information 430 may include a geographic identifier (e.g., zip code or area code) that may correspond to the IP address associated with the provider device. Other information 430 may also, or alternatively, include information identifying a type of provider (e.g., a prescription provider, a physician provider, an institutional provider, a medical equipment provider, etc.). Rule selector component 810 may obtain other information 430 from a memory or may use research tools to obtain other information 430.

Additionally, or alternatively, rule selector component 810 may receive or obtain historical information regarding the provider, the provider device, the beneficiary, or information included in the claim. In one implementation, rule selector component 710 may obtain the historical information from claims memory 620 (FIG. 6).

The claim information, the meta information, the other information, and/or the historical information may be individually referred to as a "claim attribute" or an "attribute of the claim," and collectively referred to as "claim attributes" or "attributes of the claim."

Rule selector component 810 may generate a profile for claim 410 based on the claim attributes. Based on the claim profile and perhaps relevant information in a white or black list (i.e., information, relevant to the claim, that is present in a white or black list), rule selector component 810 may select a set of libraries 710 within rules memory 630 and/or may select a set of rules within one or more of the selected libraries 710. For example, rule selector component 810 may select libraries 710, corresponding to general rules, single claim rules, multi-claim rules, provider-specific rules, procedure frequency-specific rules, etc., for claim 410.

Rule applicator component 820 may cause claim 410 to be processed using rules of the selected libraries 710. For example, rule applicator component 820 may provide information regarding claim 410 to rule engines 720 corresponding to the selected libraries 710. Each rule engine 720 may process claim 410 in parallel and may process claim 410 using all or a subset of the rules in the corresponding library 710. Claim 410 may be concurrently processed by different sets of rules (of the selected libraries 710 and/or within each of the selected libraries 710). The output, of each of the selected libraries 710, may include zero or more alarms. As explained above, an alarm may be generated when a particular rule is triggered (or satisfied).

Alarm combiner and analyzer component 830 may aggregate and correlate the alarms. For example, alarm combiner and analyzer component 830 may analyze attributes of the claim(s) with which the alarms are associated (e.g., attributes relating to a number of procedures performed, geographical information of the provider and beneficiary, a number of beneficiaries, etc.). Alarm combiner and analyzer component 830 may sort the alarms, along with alarms of other claims (past or present), into groups (called "cases") based on values of one or more of the attributes of the claims associated with the alarms (e.g., provider names, geographic locations of providers and beneficiaries, beneficiary names, etc.). The claims, included in a case, may involve one provider or multiple, unaffiliated providers and/or one beneficiary or multiple, unrelated beneficiaries.

Alarm combiner and analyzer component 830 may separate alarms (for all claims, claims sharing a common claim attribute, or a set of claims within a particular window of time) into one or more cases based on claim attributes. For example, alarm combiner and analyzer component 830 may place alarms associated with a particular claim type into a first case, alarms associated with another particular claim type into a second case, alarms associated with a particular provider into a third case, alarms associated with a beneficiary into a fourth case, alarms associated with a particular type of medical procedure into a fifth case, alarms associated with a particular geographic location into a sixth case, etc. A particular alarm may be included in multiple cases.

For example, assume that fraud detector component 650 receives four claims CL1-CL4. By processing each of claims CL1-CL4 using rules in select libraries 710, zero or more alarms may be generated. It may be assumed that three alarms A1-A3 are generated. An alarm may be an aggregation of one or more claims (e.g., alarm A1 is the aggregation of claims CL1 and CL2; alarm A2 is the aggregation of claim CL3; and alarm A3 is the aggregation of claims CL3 and CL4) that share a common attribute. The alarms may be correlated into cases. It may further be assumed that two cases C1 and C2 are formed. A case is a correlation of one or more alarms (e.g., case C1 is the correlation of alarms A1 and A2; and case C2 is the correlation of alarms A2 and A3) that share a common attribute. An individual alarm may not be sufficient evidence to determine that a claim is fraudulent. When the alarm is correlated with other alarms in a case, then a clearer picture of whether the claim is fraudulent may be obtained. Further, when multiple cases involving different attributes of the same claim are analyzed, then a decision may be made whether a claim is potentially fraudulent.

Fraud score generator component 840 may generate a fraud score. Fraud score generator component 840 may generate a fraud score from information associated with one or more cases (each of which may include one or more claims and one or more alarms). In one implementation, fraud score generator component 840 may generate an alarm score for each generated alarm. For example, each of the claim attributes and/or each of the rules may have a respective associated weight value. Thus, when a particular claim attribute causes a rule to trigger, the generated alarm may have a particular score based on the weight value of the particular claim attribute and/or the weight value of the rule. When a rule involves multiple claims, the generated alarm may have a particular score that is based on a combination of the weight values of the particular claim attributes.

In one implementation, fraud score generator component 840 may generate a case score for a case by combining the alarm scores in some manner. For example, fraud score generator component 840 may generate a case score (CS) by using a log-based Naïve Bayesian algorithm, such as:

$$CS = \frac{\sum_i \frac{AS_i \times AW_i}{AM_i}}{\sum_i AW_i} \times 1000,$$

where CS may refer to the score for a case, $AS_i$ may refer to an alarm score for a given value within an alarm i, $AW_i$ may refer to a relative weight given to alarm i, and $AM_i$ may refer to a maximum score value for alarm i. The following equation may be used to calculate $AS_i$ when the score for the alarm involves a list (e.g., more than one alarm in the case, where $s_i$ may refer to a score for alarm i):

$$AS_i = 1 - (1-s_1) \times (1-s_2) \times (1-s_n).$$

Alternatively, fraud score generator component 840 may generate a case score using an equation, such as:

$$CS = \sum_{k=1}^{m} AS_k, \text{ or}$$

$$CS = \sum_{k=1}^{m} AS_k \times AW_k.$$

Fraud score generator component 840 may generate a fraud score for a claim by combining the case scores in some manner. For example, fraud score generator component 840 may generate the fraud score (FS) using an equation, such as:

$$FS = \sum_{k=1}^{n} CS_k.$$

Alternatively, or additionally, each case may have an associated weight value. In this situation, fraud score generator component 840 may generate the fraud score using an equation, such as:

$$FS = \sum_{k=1}^{n} CS_k \times CW_k,$$

where CW may refer to a weight value for a case.

Alert generator component 850 may generate an alert or an alarm and/or a trigger based, for example, on the fraud score. In one implementation, alert generator component 850 may classify the claim, based on the fraud score, into: safe, unsafe, or for review. As described above, fraud detection unit 510 may store policies that indicate, among other things, the thresholds that are to be used to classify a claim as safe, unsafe, or for review. When the claim is classified as safe or unsafe, alert generator component 850 may generate and send the fraud score and/or an alert or alarm (e.g., safe/unsafe or accept/deny) to claims processor 280 so that claims processor 280 can make an intelligent decision as to whether to accept, deny, or fulfill the claim.

When the claim is classified as for review, alert generator component 850 may generate and send a trigger to predictive modeling unit 520 so that predictive modeling unit 520 may perform further analysis regarding a claim or a set of claims associated with a case.

Although FIG. 8 shows example functional components of fraud detector component 650, in other implementations, fraud detector component 650 may include fewer functional components, different functional components, differently arranged functional components, and/or additional functional components than those depicted in FIG. 8. Alternatively, or additionally, one or more functional components of fraud detector component 650 may perform one or more tasks described as being performed by one or more other functional components of fraud detector component 650.

Figure 9:
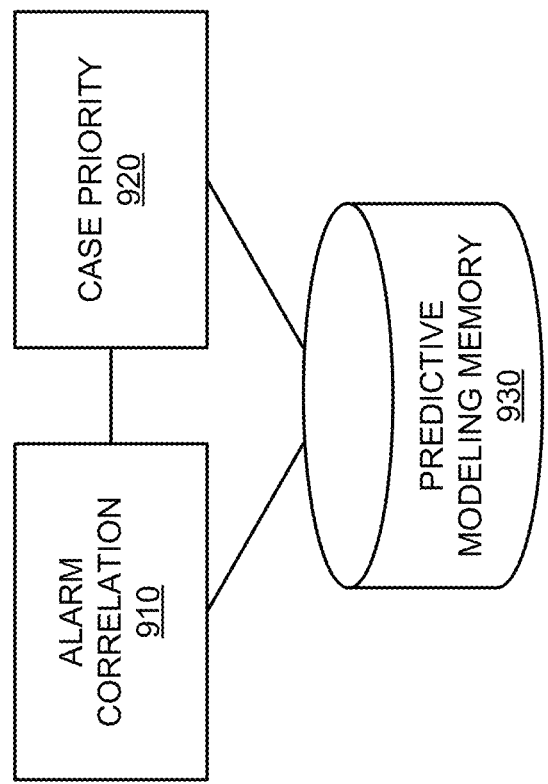
FIG. 9 is a diagram of example functional components of a predictive modeling unit of FIG. 5.

FIG. 9 is a diagram of example functional components of predictive modeling unit 520. In one implementation, the functions described in connection with FIG. 9 may be performed by one or more components of device 300 (FIG. 3) or by one or more devices 300. As shown in FIG. 9, predictive modeling unit 520 may include an alarm correlation component 910, a case priority component 920, and a predictive modeling memory 930.

Alarm correlation component 910 may correlate one or more alerts or alarms (past or present), into groups (called "cases") based on values of one or more of the attributes of the claims associated with the alarms (e.g., provider types, provider names, beneficiary names, etc.). The claims, included in a case, may involve one provider or multiple, unaffiliated providers and/or one beneficiary or multiple, unrelated beneficiaries. In one example, alarm correlation component 910 may correlate one or more alarms into cases based on a particular provider (e.g., as identified by NPI of the provider). In another example, alarm correlation component 910 may correlate one or more alarms into cases based on a particular beneficiary (e.g., as identified by a health insurance contract number (HICN) of the beneficiary). In still another example, alarm correlation component 910 may correlate one or more alarms into cases based on an address (e.g., street, zip code, etc.) associated with a particular provider. Alarm correlation component 910 may correlate one or more alarms across multiple claim types (e.g., a prescription claim, a medical procedure claim, etc.) for trend and link analysis.

In one implementation, alarm correlation component 910 may generate an alarm score for each generated alarm. For example, each alarm may include a value, and alarm correlation component 910 may utilize the value and other parameters to generate a score for each alarm. In one example, each of the claim attributes and/or each of the rules may have a respective associated weight value. Thus, when a particular claim attribute causes a rule to trigger, the generated alarm may have a particular score based on the weight value of the particular claim attribute and/or the weight value of the rule. When a rule involves multiple claims, the generated alarm may have a particular score that is based on a combination of the weight values of the particular claim attributes. In one implementation, alarm correlation component 910 may generate a case score for a case by combining the alarm scores in some manner. For example, alarm correlation component 910 may generate a case score by using a log-based Naïve Bayesian algorithm.

Case priority component 920 may receive alarm scores and/or case scores from alarm correlation component 910, and may prioritize a particular case based on a sum of alarm scores associated with the particular case or based on the case score of the particular case. Case priority component

920 may increase a case score if the claim associated with the case score includes high risk medical procedure codes and/or provider specialties (e.g., physical therapy, psychotherapy, chiropractic procedures, podiatry, ambulance services, pain management services, etc.). Case priority component 920 may increase a case score as the cost of the claim associated with the case score increases. Case priority component 920 may increase a case score if claims associated with the case contain newly-enrolled providers or if suspect geographical locations (e.g., geographically disperse provider and beneficiary) are associated with the case claims.

Predictive modeling memory 930 may include one or more memory devices to store information regarding predictive modeling tools that may be applicable to alarms, alarm scores, case scores, and/or prioritized cases generated by alarm correlation component 910 or case priority component 920. In one implementation, predictive modeling memory 930 may store claim type-specific predictive models, configurable edit rules, artificial intelligence techniques, and/or fraud scores that may be utilized by alarm correlation component 910 and/or case priority component 920 to present a prioritized list of cases for investigation so that claims 410 with the highest risk of fraud may be addressed first. The predictive models stored in predictive modeling memory 930 may support linear pattern recognition techniques (e.g., heuristics, expert rules, etc.) and non-linear pattern recognition techniques (e.g., neural nets, clustering, artificial intelligence, etc.).

Although FIG. 9 shows example functional components of predictive modeling unit 520, in other implementations, predictive modeling unit 520 may include fewer functional components, different functional components, differently arranged functional components, and/or additional functional components than those depicted in FIG. 9. Alternatively, or additionally, one or more functional components of predictive modeling unit 520 may perform one or more tasks described as being performed by one or more other functional components of predictive modeling unit 520.

Figure 10:
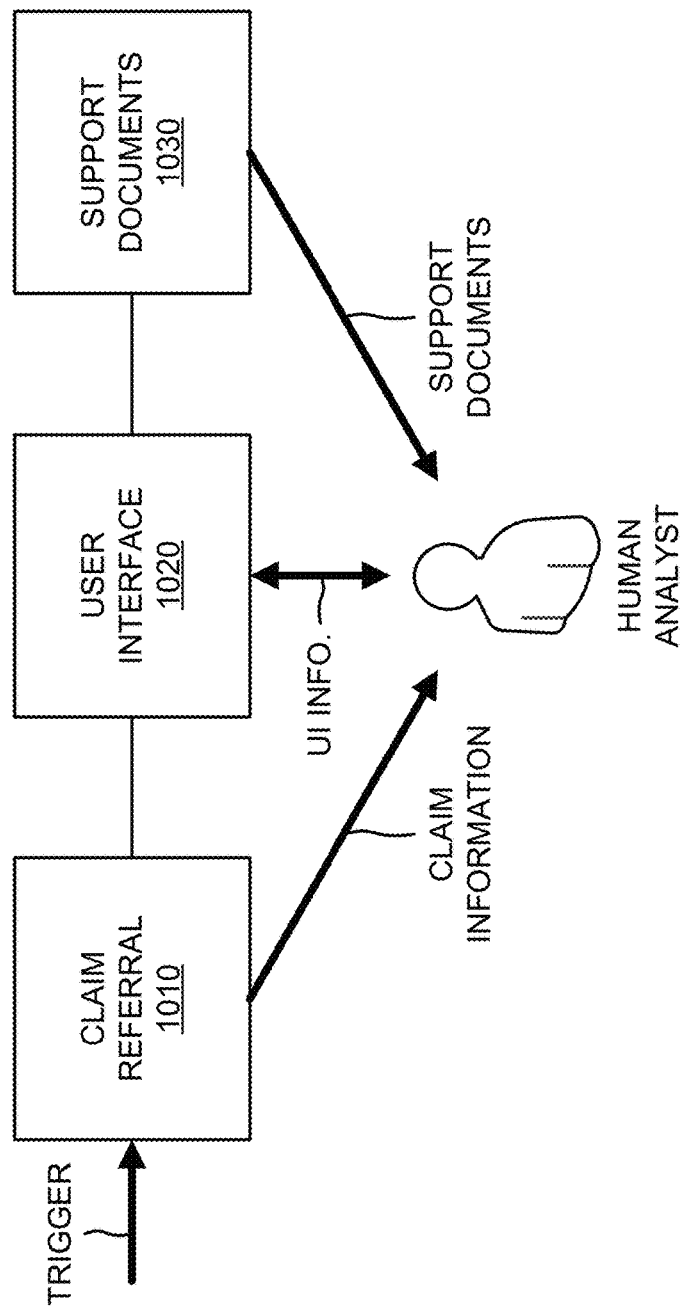
FIG. 10 is a diagram of example functional components of a fraud management unit of FIG. 5.

FIG. 10 is a diagram of example functional components of fraud management unit 530. In one implementation, the functions described in connection with FIG. 10 may be performed by one or more components of device 300 (FIG. 3) or by one or more devices 300. As shown in FIG. 10, fraud management unit 530 may include a claim referral component 1010, a user interface 1020, and a support documents component 1030.

Claim referral component 1010 may receive a trigger from alert generator 850 (FIG. 8) that indicates a particular claim is to be further reviewed for fraud. Based on the trigger, claim referral component 1010 may determine an appropriate human analyst to which to route claim information. In one implementation, claim referral component 1010 may route the claim information (e.g., including alarms, fraud scores, etc.) to a next available human analyst. Alternatively, or additionally, claim referral component 1010 may route the claim information to a human analyst with expertise in handling the particular type of claim. Routing a claim to an appropriate human analyst may improve productivity and streamline healthcare claim processing.

The human analyst may include a person, or a set of people (e.g., licensed clinicians, medical directors, data analysts, certified coders, etc.), trained to research and detect fraudulent claims. The human analyst may analyze "for review" claims (e.g., claims included in consolidated cases) and may perform research to determine whether the claims are fraudulent. Additionally, or alternatively, the human analyst may perform trending analysis, perform feedback analysis, modify existing rules, and/or create new rules. The human analyst may record the results of claim analysis and may present the results to fraud management unit 530 (e.g., via a user interface 1020) and/or claims processor 280.

User interface 1020 may include a graphical user interface (GUI) or a non-graphical user interface, such as a text-based interface. User interface 1020 may provide information to users (e.g., human analyst) of healthcare fraud management system 260 via a customized interface (e.g., a proprietary interface) and/or other types of interfaces (e.g., a browser-based interface). User interface 1020 may receive user inputs via one or more input devices, may be user configurable (e.g., a user may change the size of user interface 1020, information displayed in user interface 1020, color schemes used by user interface 1020, positions of text, images, icons, windows, etc., in user interface 1020, etc.), and/or may not be user configurable. User interface 1020 may be displayed to a user via one or more output devices.

In one implementation, user interface 1020 may be a web-based user interface that provides user interface (UI) information associated with healthcare fraud. For example, user interface 1020 may support visual graphic analysis through link analysis and geo-mapping techniques that display relationships between providers and beneficiaries. User interface 1020 may provide a fraud management desktop that displays prioritized cases for near real-time, pre-payment review with integrated workflow and queue management. The fraud management desktop may include a case summary section that lists prioritized cases with supporting aggregated data, and a case detail section that displays alerts and associated events for a selected case. The fraud management desktop may also display map locations for a provider and/or beneficiary associated with a case or claim under review. The human analyst may utilize user interface 1020 to update rule libraries 610 (e.g., thresholds, priority values, etc.) to eliminate or reduce false alarms and to ensure that the highest-risk cases receive immediate attention.

Support documents component 1030 may provide support documents to the human analyst. The support documents may include information such as case activity tracking, notes, external documents, documents that support the medical appeal process and any law enforcement intervention, etc. The support documents may be used by the human analyst to analyze and continuously improve the rules, predictive models, and other techniques used by healthcare fraud management system 260 to identify fraudulent healthcare claims.

Although FIG. 10 shows example functional components of fraud management unit 530, in other implementations, fraud management unit 530 may include fewer functional components, different functional components, differently arranged functional components, and/or additional functional components than those depicted in FIG. 10. Alternatively, or additionally, one or more functional components of fraud management unit 530 may perform one or more tasks described as being performed by one or more other functional components of fraud management unit 530.

Figure 11:
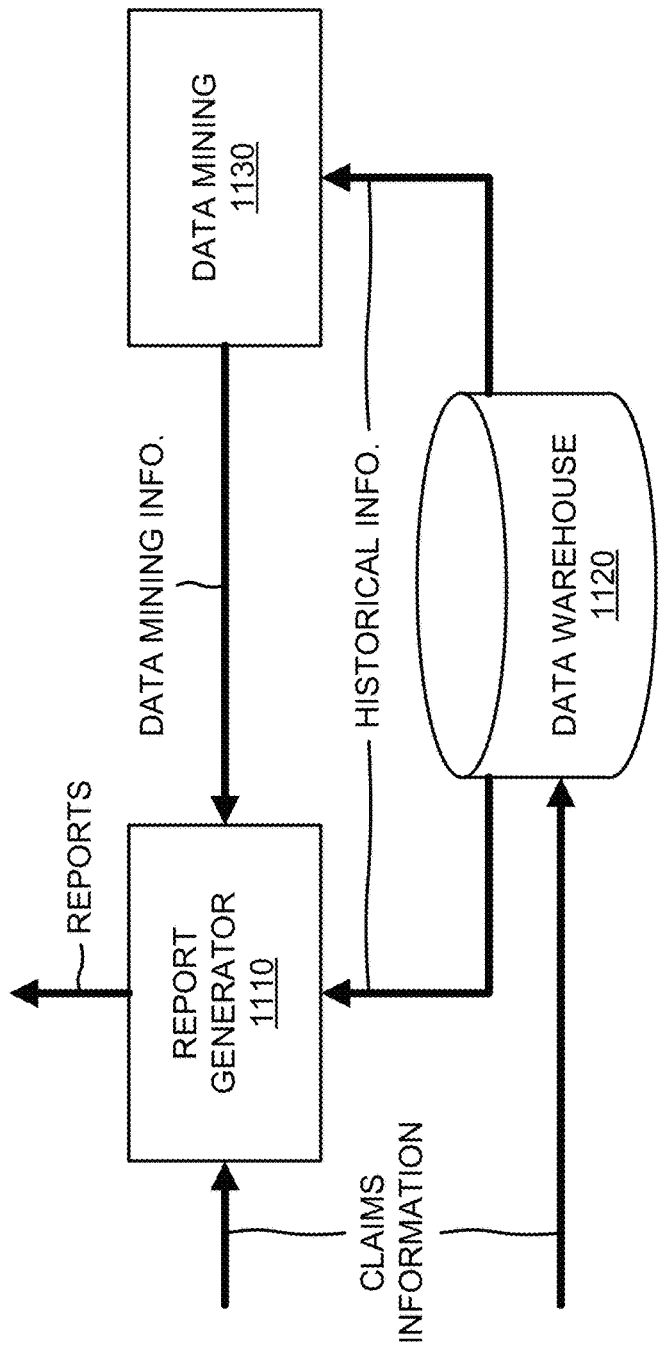
FIG. 11 is a diagram of example functional components of a reporting unit of FIG. 5.

FIG. 11 is a diagram of example functional components of reporting unit 540. In one implementation, the functions described in connection with FIG. 11 may be performed by one or more components of device 300 (FIG. 3) or by one or more devices 300. As shown in FIG. 11, reporting unit 540 may include a report generator component 1110, a data warehouse 1120, and a data mining component 1130.

Report generator component 1110 may receive claims information 420 from clearinghouse 270, may receive historical information from data warehouse 1120, and may receive data mining information from data mining component 1130. The historical information may include historical records of claims from providers, records associated with claims that were processed by a system other than healthcare fraud management system 260, information regarding claims that had been identified as fraudulent, etc. The data mining information may include extracted patterns from the historical information. Report generator 1110 may generate regular operational and management reports, weekly reports with a list of high priority suspect cases, etc. based on claims information 420, the historical information, and/or the data mining information. The regular operational and management reports may include financial management reports, trend analytics reports, return on investment reports, KPI/performance metrics reports, intervention analysis/effectiveness report, etc.

Data warehouse 1120 may include one or more memory devices to store the claims information (e.g., claims information 420) and the historical information. Information provided in data warehouse 1120 may include alerts and case management data associated with healthcare claims. Such information may be available to claims analysts for trending, post data analysis, and additional claims development, such as preparing a claim for submission to PSCs and other authorized entities.

Data mining component 1130 may receive the historical information from data warehouse 1120 and may perform data mining techniques on the historical information. The data mining techniques may include clustering, classification, regression, and association rule learning. Clustering may include discovering groups and structures in the data that are in some way or another similar, without using known structures in the data. Classification may include generalizing a known structure to apply to new data (e.g., using decision tree learning, nearest neighbor, log-based Naïve Bayesian classification, neural networks, and support vector machines). Regression may include attempting to locate a function that models the data with the least error. Association rule learning may include searches for relationships between variables. Based on the data mining techniques, data mining component 1130 may generate the data mining information that is provided to report generator component 1110.

Although FIG. 11 shows example functional components of reporting unit 540, in other implementations, reporting unit 540 may include fewer functional components, different functional components, differently arranged functional components, and/or additional functional components than those depicted in FIG. 11. Alternatively, or additionally, one or more functional components of reporting unit 540 may perform one or more tasks described as being performed by one or more other functional components of reporting unit 540.

Figure 12:
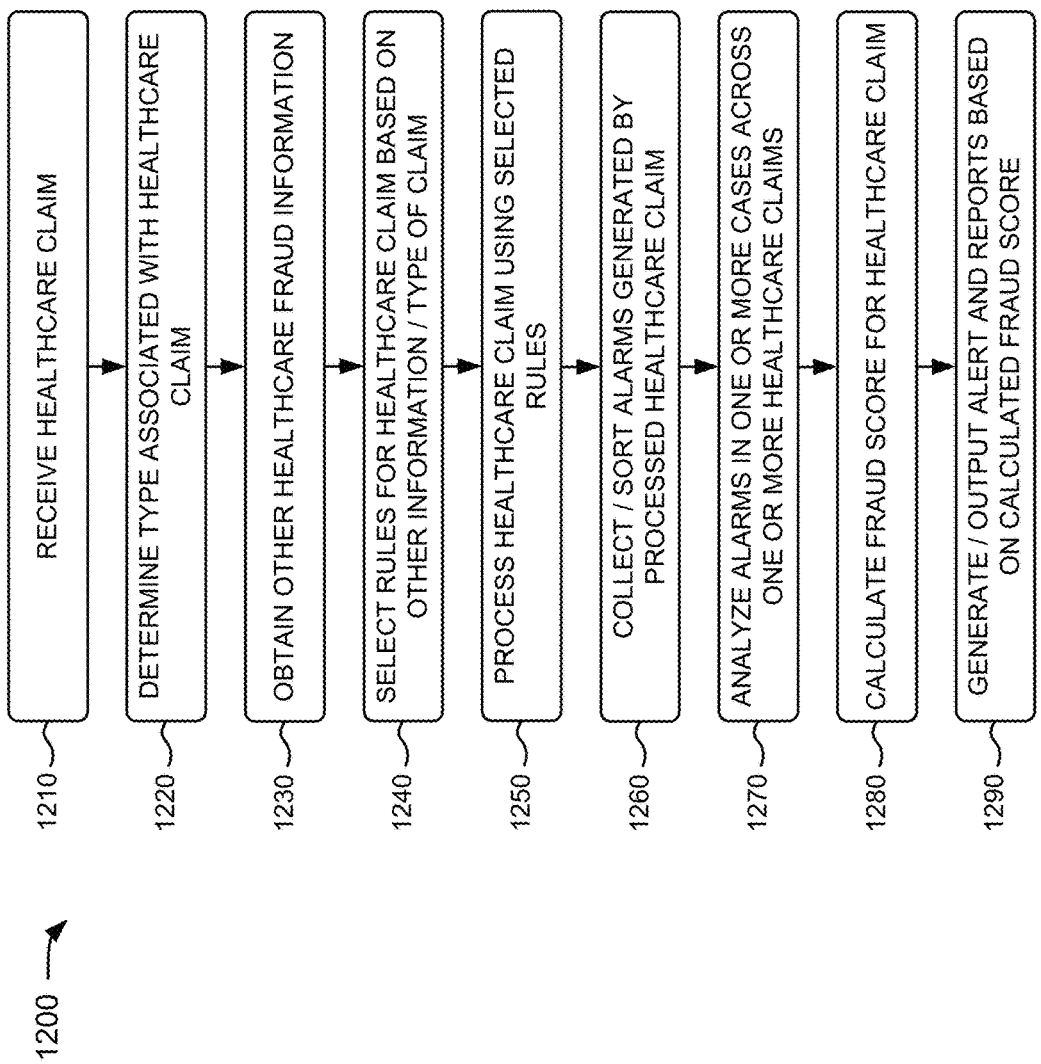
FIG. 12 is a flowchart of an example process for analyzing instances of healthcare fraud.

FIG. 12 is a flowchart of an example process 1200 for analyzing instances of healthcare fraud. In one implementation, process 1200 may be performed by one or more components/devices of healthcare fraud management system 260. Alternatively, or additionally, one or more blocks of process 1200 may be performed by one or more other components/devices, or a group of components/devices including or excluding healthcare fraud management system 260.

Process 1200 may include receiving a healthcare claim (block 1210). For example, fraud detector component 650 may receive, from clearinghouse 270, a claim involving a provider and a beneficiary. Clearinghouse 270 may use secure communications, such as encryption or a VPN, to send the claim to healthcare fraud management system 260. In one implementation, clearinghouse 270 may send the claim to healthcare fraud management system 260 in near real-time (e.g., after the provider submits the claim to clearinghouse 270) and perhaps prior to payment of the claim. Alternatively, or additionally, clearinghouse 270 may send the claim to healthcare fraud management system 260 after payment of the claim (e.g., after claims processor 280 has provided money to the provider for the claim). In practice, healthcare fraud management system 260 may simultaneously receive information regarding multiple claims from clearinghouse 270.

A type associated with the healthcare claim may be determined (block 1220). For example, rule selector component 810 may determine a type (e.g., a prescription provider claim, a physician provider claim, an institutional provider claim, a medical equipment provider claim, etc.) associated with claim 410.

Other healthcare fraud information may be obtained (block 1230). For example, healthcare fraud management system 260 may obtain other information 430 regarding healthcare fraud from other systems. Other information 430 may include information associated with providers under investigation for possible fraudulent activities, information associated with providers who previously committed fraud, information provided by ZPICs, information provided by recovery audit contractors, and information provided by other external data sources. The information provided by the other external data sources may include an excluded provider list (EPL), a federal investigation database (FID), compromised provider and beneficiary identification (ID) numbers, compromised number contractor (CNC) information, benefit integrity unit (BIU) information, provider enrollment (PECOS) system information, and information from common working file (CWF) and claims adjudication systems.

Rules may be selected for the healthcare claim based on the other information and the type of claim (block 1240). For example, rule selector component 810 may generate a profile for claim 410 based on the claim attributes (e.g., claim type, other information 430, etc.). Based on the claim profile and perhaps relevant information in a white or black list (i.e., information, relevant to the claim, that is present in a white or black list), rule selector component 810 may select a set of libraries 710 within rules memory 630 and/or may select a set of rules within one or more of the selected libraries 710. In one example, rule selector component 810 may select libraries 710, corresponding to general rules, single claim rules, multi-claim rules, provider-specific rules, procedure frequency-specific rules, etc., for claim 410.

The healthcare claim may be processed using the selected rules (block 1250). For example, fraud detector component 650 may provide the claim to rule engines 720 corresponding to the selected set of libraries 710 for processing. In one implementation, fraud detector component 650 may provide the claim for processing by multiple rule engines 720 in parallel. The claim may also be processed using two or more of the rules, in the selected set of rules of a library 710, in parallel. By processing the claim using select rules, the accuracy of the results may be improved over processing the claim using all of the rules (including rules that are irrelevant to the claim). When a rule triggers (is satisfied), an alarm may be generated. The output of processing the claim using the selected rules may include zero or more alarms.

Alarms generated by the processed healthcare claim may be collected and sorted (block 1260). For example, fraud detector component 650 may aggregate the alarms and may analyze attributes of the claims with which the alarms are associated (e.g., attributes relating to a particular form of payment, a particular geographic area, a particular consumer, etc.). Fraud detector component 650 may correlate the alarms, along with alarms of other claims (past or present associated with the same or different (unaffiliated) providers), into cases based on values of the attributes of the claims associated with alarms. For example, fraud detector component 650 may include one or more alarms associated with a particular beneficiary in a first case, one or more alarms associated with a particular provider location in a second case, one or more alarms associated with a particular medical procedure in a third case, etc. As described above, a particular alarm may be included in multiple cases.

The alarms, in one or more cases, may be analyzed across one or more healthcare claims (block 1270). For example, fraud detector component 650 may analyze the alarms in a case (where the alarms may be associated with multiple claims possibly from multiple, unaffiliated providers and/or possibly from multiple, different beneficiaries) to determine whether the alarms justify a determination that the claim is potentially fraudulent. By analyzing alarms in multiple cases, fraud detector component 650 may get a good picture of whether fraudulent activity is occurring.

A fraud score for the healthcare claim may be calculated (block 1280). For example, fraud detector component 650 may generate a case score for each of the cases using a technique, such as a technique described previously. Fraud detector component 650 may combine the case scores, associated with the claim, to generate a fraud score for the claim. In one implementation, as described above, the case scores, associated with the different cases, may be weighted differently. For example, the fraud score of case 1 may have an associated weight of CW1, the fraud score of case 2 may have an associated weight of CW2, the fraud score of case 3 may have an associated weight of CW3, etc. Thus, in this implementation, the different case scores may not contribute equally to the fraud score. The fraud score may reflect a probability that the claim is fraudulent.

In one implementation, the fraud score may include a value in the range of 0 to 100, where "0" may reflect a 0% probability that the claim is fraudulent and "100" may reflect a 100% probability that the claim is fraudulent. It may be possible for the case score of a particularly important case (with a high weight value) to drive the fraud score to 100 (even without any contribution from any other cases).

An alert and/or reports may be generated and outputted based on the calculated fraud score (block 1290). For example, fraud detector component 650 may generate an alert based on the fraud score and policies associated with clearinghouse 270 and/or claims processor 280. For example, clearinghouse 270 and/or claims processor 280 may specify policies that indicate what fraud scores constitute a safe claim, what fraud scores constitute an unsafe claim, and what fraud scores constitute a for review claim. Fraud detector component 650 may generate an alert that indicates, to claims processor 280, that the claim should be permitted or that the claim should be denied.

Fraud detector component 650 may send the alert and/or the fraud score to clearinghouse 270 and/or claims processor 280 for processing the claim accordingly. In one implementation, fraud detector component 650 may send the alert and/or fraud score while it is still processing the claim (e.g., before claims processor 280 has approved the claim). Alternatively, or additionally, fraud detector component 650 may send the alert and/or fraud score after claims processor 280 has completed processing the claim (e.g., after claims processor 280 has approved the claim). In the latter implementation, when the claim is determined to be potentially fraudulent, claims processor 280 may take measures to minimize its loss (e.g., by canceling the payment of a medical claim, etc.).

Figure 13:
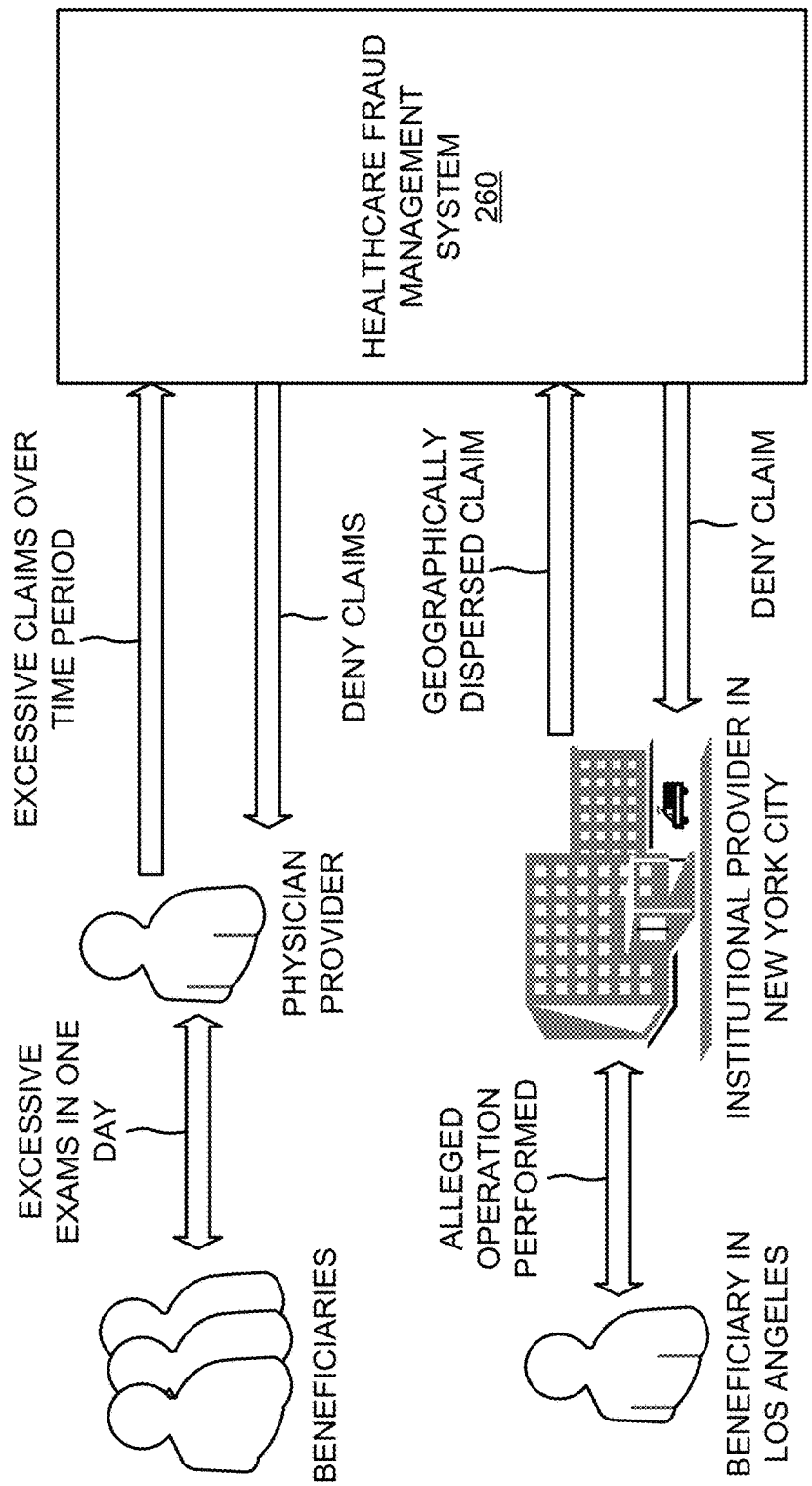
FIG. 13 is a diagram illustrating an example for identifying a fraudulent healthcare claim.

FIG. 13 is a diagram illustrating an example for identifying a fraudulent healthcare claim. As shown in FIG. 13, a physician provider may perform an excessive number of examinations in one day for beneficiaries. For example, the physician provider may allegedly perform thirty (30) hours of examinations in a single day. The physician provider may submit, to healthcare fraud management system 260, an excessive number of claims that correspond to the excessive number of examinations performed in a time period (e.g., one day). Healthcare fraud management system 260 may receive the excessive claims, and may process the excessive claims. For example, healthcare fraud management system 260 may obtain other information 430 relevant to the excessive claims, may select rules for the claims, such as beneficiary frequency-specific rules, and may process the claims using the selected rules. Assume that a set of the selected rules trigger and generate corresponding alarms. For example, one rule may generate an alarm because the physician provider has treated an excessive number of beneficiaries in a particular time period.

Healthcare fraud management system 260 may process the alarms and determine, for example, that the excessive claims are potentially fraudulent based on the information known to healthcare fraud management system 260. Healthcare fraud management system 260 may notify clearinghouse 270 or claims processor 280 (not shown) that the excessive claims are potentially fraudulent, and may instruct clearinghouse 270 or claims processor 280 to deny the excessive claims.

As further shown in FIG. 13, a beneficiary located in Los Angeles, Calif. may have a procedure performed in Los Angeles, and may have an operation performed by an institutional provider located in New York City, N.Y. on the same day. The institutional provider may submit, to healthcare fraud management system 260, a geographically dispersed claim that corresponds to the alleged operation performed for the remotely located beneficiary. Healthcare fraud management system 260 may receive the geographically dispersed claim, and may process the geographically dispersed claim. For example, healthcare fraud management system 260 may obtain other information 430 relevant to the geographically dispersed claim, may select rules for the claims, such as geographical dispersion of services-specific rules, and may process the claim using the selected rules. Assume that a set of the selected rules trigger and generate corresponding alarms. For example, one rule may generate an alarm because the beneficiary in Los Angeles receives a service from the Los Angeles provider and from the New York City provider on the same day. In other words, it may be highly unlikely that person living in Los Angeles would have procedures done in Los Angeles and in New York City on the same day.

Healthcare fraud management system 260 may process the alarms and determine, for example, that the geographically dispersed claim is potentially fraudulent based on the information known to healthcare fraud management system 260. Healthcare fraud management system 260 may notify clearinghouse 270 or claims processor 280 (not shown) that the geographically dispersed claim is potentially fraudulent, and may instruct clearinghouse 270 or claims processor 280 to deny the geographically dispersed claim.

The foregoing description provides illustration and description, but is not intended to be exhaustive or to limit the invention to the precise form disclosed. Modifications and variations are possible in light of the above disclosure or may be acquired from practice of the invention.

For example, while a series of blocks has been described with regard to FIG. 12, the order of the blocks may be modified in other implementations. Further, non-dependent blocks may be performed in parallel.

It will be apparent that different aspects of the description provided above may be implemented in many different forms of software, firmware, and hardware in the implementations illustrated in the figures. The actual software code or specialized control hardware used to implement these aspects is not limiting of the invention. Thus, the operation and behavior of these aspects were described without reference to the specific software code—it being understood that software and control hardware can be designed to implement these aspects based on the description herein.

Even though particular combinations of features are recited in the claims and/or disclosed in the specification, these combinations are not intended to limit the disclosure of the invention. In fact, many of these features may be combined in ways not specifically recited in the claims and/or disclosed in the specification. Although each dependent claim listed below may directly depend on only one other claim, the disclosure of the invention includes each dependent claim in combination with every other claim in the claim set.

No element, act, or instruction used in the present application should be construed as critical or essential to the invention unless explicitly described as such. Also, as used herein, the article "a" is intended to include one or more items and may be used interchangeably with 'one or more. Where only one item is intended, the term "one" or similar language is used. Further, the phrase "based on" is intended to mean "based, at least in part, on" unless explicitly stated otherwise.

What is claimed is:

1. A system, comprising:
    a first device to:
        identify first information associated with a second device;
        generate a first value for one or more indicators associated with the first information,
            the first value being generated by performing one or more mathematical operations on a plurality of values;
        process the first information using a rule to generate a combined value,
            the first device, when processing the first information, being to:
                provide the first information to a rules engine corresponding to a library of rules,
                    the library of rules including the rule, and
                receive, from the rules engine and based on providing the first information to the rules engine, second information associated with the combined value,
                    the combined value being based on combining the first value with one or more third values;
        output, based on processing the first information, the second information for processing a first claim,
            the first claim to be approved, and
            the second information including a first alarm;
        receive third information regarding a second claim after the first claim is processed;
        process the third information using one or more rules of the library of rules;
        generate, based on processing the third information, a second alarm associated with the second claim;
        correlate the first alarm and the second alarm based on attributes of the first claim and attributes of the second claim; and
        generate, based on correlating the first alarm and the second alarm, an alert regarding the first claim,
            a payment of the first claim being canceled, after the first claim has been approved, based on the alert.

2. The system of claim 1, where the first device is further to:
    select the rule,
        the rule being selected based on a profile associated with the first information.

3. The system of claim 2, where the profile is based on at least one of:
    meta information associated with the first information, or
    historical information associated with the first information.

4. The system of claim 1, where the first device is further to:
    generate the first alarm based on the combined value.

5. The system of claim 1, where the first device, when processing the first information, is to:
    process the first information using the rule to generate a plurality of alarms;
    sort the plurality of alarms into a plurality of groups based on attributes of the first information; and
    analyze the plurality of groups to generate the combined value.

6. The system of claim 1, where the first device is further to:
    analyze the combined value with respect to a first threshold and a second threshold;
    classify the first information as a first type of information when the combined value is less than the first threshold; and
    classify the first information as a second type of information when the combined value is greater than the second threshold.

7. The system of claim 1, where the second information is outputted in near real-time.

8. A method, comprising:
    identifying, by a first device, first information associated with a second device;
    generating, by the first device, a first value for one or more indicators associated with the first information,
        the first value being generated by performing one or more mathematical operations on a plurality of values;
    processing, by the first device, the first information using a rule to generate a combined value,
        the processing the first information including:
            providing the first information to a rules engine corresponding to a library of rules,
                the library of rules including the rule; and
            receiving, from the rules engine and based on providing the first information to the rules engine, second information associated with the combined value,
                the combined value being based on combining the first value with one or more third values;

outputting, by the first device and based on processing the first information, the second information for processing a first claim,
  the first claim to be approved, and
  the second information including a first alarm;
receiving, by the first device, third information regarding a second claim after the first claim is processed;
processing, by the first device, the third information using one or more rules of the library of rules;
generating, by the first device and based on processing the third information, a second alarm associated with the second claim;
correlating, by the first device, the first alarm and the second alarm based on attributes of the first claim and attributes of the second claim; and
generating, by the first device and based on correlating the first alarm and the second alarm, an alert regarding the first claim,
  a payment of the first claim being canceled, after the first claim has been approved, based on the alert.

9. The method of claim 8, further comprising:
selecting the rule,
  the rule being selected based on a profile associated with the first information.

10. The method of claim 9, where the profile is based on at least one of:
meta information associated with the first information, or
historical information associated with the first information.

11. The method of claim 8, further comprising:
generating the first alarm based on the combined value.

12. The method of claim 8, where processing the first information includes:
processing the first information using the rule to generate a plurality of alarms;
sorting the plurality of alarms into a plurality of groups based on attributes of the first information; and
analyzing the plurality of groups to generate the combined value.

13. The method of claim 8, further comprising:
analyzing the combined value with respect to a first threshold and a second threshold;
classifying the first information as a first type of information when the combined value is less than the first threshold; and
classifying the first information as a second type of information when the combined value is greater than the second threshold.

14. The method of claim 8, where the second information is outputted in near real-time.

15. A non-transitory computer-readable medium storing instructions, the instructions comprising:
one or more instructions which, when executed by a processor of a device, cause the processor to:
  identify first information associated with a second device;
  generate a first value for one or more indicators associated with the first information,
    the first value being generated by performing one or more mathematical operations on a plurality of values;
  process the first information using a rule to generate a combined value,
    the one or more instructions, when executed by the processor to process the first information, cause the processor to:
      provide the first information to a rules engine corresponding to a library of rules,
        the library of rules including the rule, and
      receive, from the rules engine and based on providing the first information to the rules engine, second information associated with the combined value, and
        the combined value being based on combining the first value with one or more third values;
  output, based on processing the first information, the second information for processing a first claim,
    the first claim to be approved, and
    the second information including a first alarm;
  receive third information regarding a second claim after the first claim is processed;
  process the third information using one or more rules of the library of rules;
  generate, based on processing the third information, a second alarm associated with the second claim;
  correlate the first alarm and the second alarm based on attributes of the first claim and attributes of the second claim; and
  generate, based on correlating the first alarm and the second alarm, an alert regarding the first claim,
    a payment of the first claim being canceled, after the first claim has been approved based on the alert.

16. The non-transitory computer-readable medium of claim 15, where the one or more instructions, when executed by the processor, further cause the processor to:
select the rule,
  the rule being selected based on a profile associated with the first information.

17. The non-transitory computer-readable medium of claim 16, where the profile is based on at least one of:
meta information associated with the first information, or
historical information associated with the first information.

18. The non-transitory computer-readable medium of claim 15, where the one or more instructions, when executed by the processor, further cause the processor to:
generate the first alarm based on the combined value.

19. The non-transitory computer-readable medium of claim 15, where the one or more instructions, that cause the processor to process the first information, cause the processor to:
process the first information using the rule to generate a plurality of alarms;
sort the plurality of alarms into a plurality of groups based on attributes of the first information; and
analyze the plurality of groups to generate the combined value.

20. The non-transitory computer-readable medium of claim 15, where the one or more instructions, when executed by the processor, further cause the processor to:
analyze the combined value with respect to a first threshold and a second threshold;
classify the first information as a first type of information when the combined value is less than the first threshold; and
classify the first information as a second type of information when the combined value is greater than the second threshold.

* * * * *